(12) United States Patent
Thompson et al.

(10) Patent No.: US 8,785,624 B2
(45) Date of Patent: Jul. 22, 2014

(54) ORGANIC PHOTOSENSITIVE OPTOELECTRONIC DEVICES WITH NONPLANAR PORPHYRINS

(75) Inventors: Mark E. Thompson, Anaheim, CA (US); Maria Dolores Perez, Marina Del Rey, CA (US); Carsten Borek, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 1475 days.

(21) Appl. No.: 11/762,492

(22) Filed: Jun. 13, 2007

(65) Prior Publication Data

US 2008/0311304 A1     Dec. 18, 2008

(51) Int. Cl.
C07D 487/02     (2006.01)
C07B 47/00      (2006.01)

(52) U.S. Cl.
USPC .......................................................... 540/145

(58) Field of Classification Search
USPC ................................ 428/411.1, 913; 540/145
See application file for complete search history.

(56) References Cited

U.S. PATENT DOCUMENTS

| 6,352,777 B1 * | 3/2002 | Bulovic et al. ............. 428/411.1 |
| 6,580,027 B2 | 6/2003 | Forrest et al. |
| 6,657,378 B2 | 12/2003 | Forrest et al. |
| 2005/0072971 A1 | 4/2005 | Marrocco |
| 2006/0278944 A1 | 12/2006 | Rand |

FOREIGN PATENT DOCUMENTS

| EP | 1 811 573 A | 7/2007 |
| JP | 58190074 A | 11/1983 |
| JP | 2004327166 A | 11/2004 |
| WO | WO 2006/018475 | 2/2006 |
| WO | WO 2006/051874 | 5/2006 |

OTHER PUBLICATIONS

Peumans et al., "Small molecular weight organic thin-film photodetectors and solar cells", J. Appl. Phys. (93)7: 3693-3723, 2003.
Singh et al., "Copper-phthalocyanine-based organic solar cells with high open-circuit voltage", Appl. Phys. Lett. 86(8): 082106, 2005.
Brabec et al., "Origin of the open circuit voltage of plastic solar cells", Adv. Functional Mater. 11(5): 374-380, 2001.
Gledhill et al., "Organic and nano-structured composite photovoltaics: An overview", J. Mater. Res. 20(12): 3167-3179, 2005.
Mutolo et al., "Enhanced open-circuit voltage in subphthalocyanine/C-60 organic photovoltaic cells", J. of the American Chemical Society 128(25): 8108-8109, 2006.
Terao et al., "Correlation of hole mobility, exciton diffusion length, and solar cell characteristics in phthalocyanine/fullerene organic solar cells", Appl. Phys. Lett. 90(10): 103515, 2007.
Borek et al., "Highly efficient, near-infrared electrophosphorescence from a Pt-Metalloporphyrin complex", Angewandte Chemie International Edition 46(7): 1109-1112, 2007.
Burrows et al., "Relationship between electroluminescence and current transport in organic heterojunction light-emitting devices", J. Appl. Phys. 79(10): 7991-8006, 1996.
Bredas et al., "Chain-length dependence of electronic and electrochemical properties of conjugated systems—polyacetylene, polyphenylene, polythiophene, and polypyrrole", J. of the American Chemical Society 105(22): 6555-6559, 1983.
D'Andrade et al., "Relationship between the ionization and oxidation potentials of molecular organic semiconductors", Organic Electronics 6(1): 11-20, 2005.
Retsek J L et al, "Conformational and electronic effects of phenyl-ring fluorination on the photophysical properties of nonplanar dodecaarylporphyrins" Journal of Physical Chemistry B, vol. 105, No. 27, Jul. 12, 2001, pp. 6396-6411, XP002494116 American Chemical Society US, published on the Web Jun. 16, 2001 Scheme 1 p. 6405, line 9-line 11.
Sazanovich, I.V. et al, "Photophysical and Structural Properties of Saddle-Shaped Free Base Porphyrins: Evidence of an "Orthogonal" Dipole Moment" Journal of Physical Chemistry B, vol. 105, No. 32, Jul. 20, 2001, pp. 7818-7829, XP002494115 American Chemical Society, published on the Web Jul. 20, 2001 figure 1.
Sun, Yiru et al, "Photophysics of Pt-porphyrin electrophosphorescent devices emitting in the near infrared" Applied Physics Letters, AIP, American Institute of Physics, Melville, NY, vol. 90, No. 21, May 21, 2007, pp. 213503-213503, XP012094989 ISSN: 0003-6951 cited in the application figure 1.

* cited by examiner

*Primary Examiner* — Paul V. Ward
(74) *Attorney, Agent, or Firm* — Finnegan, Henderson, Farabow, Garrett & Dunner LLP

(57) ABSTRACT

Embodiments of the present invention provide an organic photosensitive optoelectronic device comprising at least one nonplanar porphyrin of formula (I),

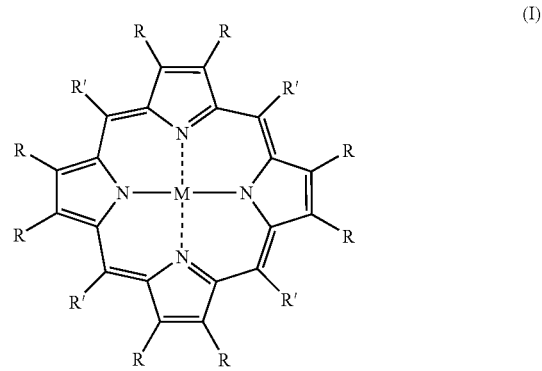

(I)

wherein the meanings of M, R and R' are disclosed herein.

46 Claims, 10 Drawing Sheets

ORGANIC PHOTOSENSITIVE OPTOELECTRONIC DEVICES WITH NONPLANAR PORPHYRINS

JOINT RESEARCH AGREEMENT

The claimed invention was made by, on behalf of, and/or in connection with the following parties to a joint university-corporation research agreement: The University of Southern California and Global Photonic Energy Corporation. The agreement was in effect on and before the date the claimed invention was made, and the claimed invention was made as a result of activities undertaken within the scope of the agreement.

FIELD OF THE INVENTION

The present invention generally relates to organic photosensitive optoelectronic devices. More specifically, it is directed to organic photosensitive optoelectronic devices comprising at least one nonplanar porphyrin.

BACKGROUND

Optoelectronic devices rely on the optical and electronic properties of materials to either produce or detect electromagnetic radiation electronically or to generate electricity from ambient electromagnetic radiation.

Photosensitive optoelectronic devices convert electromagnetic radiation into an electrical signal or electricity. Solar cells, also called photovoltaic ("PV") devices, are a type of photosensitive optoelectronic device that is specifically used to generate electrical power. Photoconductor cells are a type of photosensitive optoelectronic device that are used in conjunction with signal detection circuitry which monitors the resistance of the device to detect changes due to absorbed light. Photodetectors, which may receive an applied bias voltage, are a type of photosensitive optoelectronic device that are used in conjunction with current detecting circuits which measures the current generated when the photodetector is exposed to electromagnetic radiation.

These three classes of photosensitive optoelectronic devices may be distinguished according to whether a rectifying junction is present and also according to whether the device is operated with an external applied voltage, also known as a bias or bias voltage. A photoconductor cell does not have a rectifying junction and is normally operated with a bias. A PV device has at least one rectifying junction and is operated with no bias. A photodetector has at least one rectifying junction and is usually but not always operated with a bias.

As used herein, the term "rectifying" denotes, inter alia, that an interface has an asymmetric conduction characteristic, i.e., the interface supports electronic charge transport preferably in one direction. The term "semiconductor" denotes materials which can conduct electricity when charge carriers are induced by thermal or electromagnetic excitation. The term "photoconductive" generally relates to the process in which electromagnetic radiant energy is absorbed and thereby converted to excitation energy of electric charge carriers so that the carriers can conduct (i.e., transport) electric charge in a material. The term "photoconductive material" refers to semiconductor materials which are utilized for their property of absorbing electromagnetic radiation to generate electric charge carriers.

When electromagnetic radiation of an appropriate energy is incident upon an organic semiconductor material, a photon can be absorbed to produce an excited molecular state. In organic photoconductive materials, the generated molecular state is generally believed to be an "exciton," i.e., an electron-hole pair in a bound state which is transported as a quasi-particle. An exciton can have an appreciable life-time before geminate recombination ("quenching"), which refers to the original electron and hole recombining with each other (as opposed to recombination with holes or electrons from other pairs). To produce a photocurrent, the electron-hole forming the exciton are typically separated at a rectifying junction.

In the case of photosensitive devices, the rectifying junction is referred to as a photovoltaic heterojunction. Types of organic photovoltaic heterojunctions include a donor-acceptor heterojunction formed at an interface of a donor material and an acceptor material, and a Schottky-barrier heterojunction formed at the interface of a photoconductive material and a metal.

FIG. 1 is an energy-level diagram illustrating an example donor-acceptor heterojunction. In the context of organic materials, the terms "donor" and "acceptor" refer to the relative positions of the Highest Occupied Molecular Orbital ("HOMO") and Lowest Unoccupied Molecular Orbital ("LUMO") energy levels of two contacting but different organic materials. If the LUMO energy level of one material in contact with another is lower, then that material is an acceptor. Otherwise it is a donor. It is energetically favorable, in the absence of an external bias, for electrons at a donor-acceptor junction to move into the acceptor material.

As used herein, a first HOMO or LUMO energy level is "greater than" or "higher than" a second HOMO or LUMO energy level if the first energy level is closer to the vacuum energy level 10. A higher HOMO energy level corresponds to an ionization potential ("IP") having a smaller absolute energy relative to a vacuum level. Similarly, a higher LUMO energy level corresponds to an electron affinity ("EA") having a smaller absolute energy relative to vacuum level. On a conventional energy level diagram, with the vacuum level at the top, the LUMO energy level of a material is higher than the HOMO energy level of the same material.

After absorption of a photon 6 in the donor 152 or the acceptor 154 creates an exciton 8, the exciton 8 dissociates at the rectifying interface. The donor 152 transports the hole (open circle) and the acceptor 154 transports the electron (dark circle).

A significant property in organic semiconductors is carrier mobility. Mobility measures the ease with which a charge carrier can move through a conducting material in response to an electric field. In the context of organic photosensitive devices, a material that conducts preferentially by electrons due to a high electron mobility may be referred to as an electron transport material. A material that conducts preferentially by holes due to a high hole mobility may be referred to as a hole transport material. A layer that conducts preferentially by electrons, due to mobility and/or position in the device, may be referred to as an electron transport layer ("ETL"). A layer that conducts preferentially by holes, due to mobility and/or position in the device, may be referred to as a hole transport layer ("HTL"). Preferably, but not necessarily, an acceptor material is an electron transport material and a donor material is a hole transport material.

How to pair two organic photoconductive materials to serve as a donor and an acceptor in a photovoltaic heterojunction based upon carrier mobilities and relative HOMO and LUMO levels is well known in the art, and is not addressed here.

One common feature of bulk semiconductors, as well as insulators, is a "band gap." The band gap is the energy difference between the highest energy level filled with electrons and the lowest energy level that is empty. In an inorganic semiconductor or inorganic insulator, this energy difference is the difference between the valence band edge (top of the valence band) and the conduction band edge (bottom of the conduction band). In an organic semiconductor or organic insulator, this energy difference is the difference between the HOMO and the LUMO. The band gap of a pure material is devoid of energy states where electrons and holes can exist. The only available carriers for conduction are the electrons and holes which have enough energy to be excited across the band gap. In general, semiconductors have a relatively small band gap in comparison to insulators.

In terms of an energy band model for organic semiconductors, only electrons on the LUMO side of the band gap are charge carriers, and only holes on the HOMO side of the band gap are charge carriers.

Additional background explanation and description of the state of the art for organic photosensitive devices, including their general construction, characteristics, materials, and features, can be found in U.S. Pat. No. 6,657,378 to Forrest et al., U.S. Pat. No. 6,580,027 to Forrest et al., and U.S. Pat. No. 6,352,777 to Bulovic et al., the disclosures of which are incorporated herein by reference.

The performances of small molecular solar cells are determined by studying their characteristic IV responses under dark conditions and under illumination. The power conversion efficiency, $\eta_P$, is dependent on the open circuit voltage ($V_{oc}$), the short-circuit current density ($J_{sc}$), and the fill factor (FF) via[1]:

$$\eta_P = (J_{sc} \times V_{oc} \times FF)/P_o \quad (1)$$

where $P_o$ is the incident optical power. Here, FF depends on the series resistance and is typically between 0.5 and 0.65 for high performance small molecular weight organic photovoltaics. The maximum $J_{sc}$ is defined by the overlap between the absorption of the organics, the solar spectrum and the extinction coefficients and thicknesses of the absorbing layers and other factors. However, the photocurrent is highly dependent on the charge transport properties of the materials, since resistivity to charge flow represents a significant challenge to cell performance[2]. Another very important parameter to be considered when referring to cell performance is the exciton diffusion length. The exciton diffusion length of a material represents the distance that an exciton can travel prior to recombination. Accordingly, in order to achieve a high percentage of charge carriers relative to the number of excitons created by absorbed photons the exciton is preferably formed within about $L_D$ of a Heterojunction. The exciton diffusion length, $L_D$, is related to the exciton diffusion coefficient, D, and the exciton lifetime, $\tau$, by the expression: $L_D = \sqrt{D\tau}$. The exciton diffusion length is generally short for organic semiconductors relative to the optical absorption length $L_A$, hence limiting the thickness of the organic layer to be used due to the relatively low ability of the excitons to reach the Donor-Acceptor interface for charge separation. This effect not only restrains the amount of absorbing material but also creates a resistive pathway for separated charge that is undesirable for efficient light conversion[1].

The origin of Voc in organic solar cells is not well understood[3,4]. Some people suggest that it is mainly dependent on the energy difference between the lowest unoccupied molecular orbital (LUMO) of the acceptor-like material and the highest occupied molecular orbital (HOMO) of the donor-like material at the heterointerface in a bilayer cell (referred to as the interface gap, Ig)[5]. However others have observed no evident relation between this Ig and the Voc observed and propose that this voltage is controlled by a chemical potential gradient that would depend on the carrier mobility[6]. Yet, it is clear that the Voc does not reflect the total energy of the photons absorbed and that energy must be lost during the power conversion process. These losses have not been accounted for so far and much care must be taken when assessing the foundations of the open-circuit voltage.

SUMMARY OF THE INVENTION

The present invention provides a photosensitive optoelectronic device comprising at least one nonplanar porphyrin of formula (I),

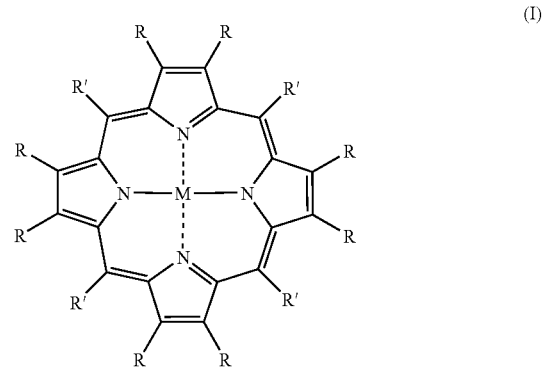

(I)

wherein

M is selected from the group consisting of Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Si, Ge, Sn, Pb, P, As, Sb, Bi, S, Se, Te, Po, Cl, Br, I, At, lanthanides, actinides and 2H;

R' is independently selected from the group consisting of a Cl atom, Br atom, I atom, At atom, and a chemical group comprising a valence atom attached to the meso carbon atom of the porphyrin, wherein the valence atom is selected from the group consisting of B, C, N, O, Si, P, S, Ge, As, Se, In, Sn, Sb, Te, Tl, Pb, Bi and Po; and R is independently selected from the group consisting of a Cl atom, Br atom, I atom, At atom, and a chemical group comprising a valence atom attached to a β carbon atom of a pyrrole ring, wherein the valence atom is selected from the group consisting of B, C, N, O, Si, P, S, Ge, As, Se, In, Sn, Sb, Te, Tl, Pb, Bi and Po, alternatively two adjacent R groups attached to the same pyrrole ring together with the two β carbon atoms of the pyrrole ring form a carbocyclic group or heterocyclic group, wherein the carbocyclic group is monocyclic or multicyclic, and the heterocyclic group is monocyclic or multicyclic.

The present invention also provides a method for fabricating the photosensitive optoelectronic device of the present invention, the method comprising providing a donor material and an acceptor material, wherein the donor material and/or the acceptor material comprises at least one nonplanar porphyrin of formula (I) of the present invention; and making the photosenstive optoelectronic device comprising putting the donor material in contact with the acceptor material, wherein when both the donor material and acceptor material comprise at least one nonplanar porphyrin of formula (I), the at least one nonplanar porphyrin in the donor material is different from the at least one nonplanar porphyrin in the acceptor material.

In addition, the present invention provides at least one of the nonplanar porphyrins of formula (I), wherein M, R' and R are as described in this patent application, useful in some or all of the embodiments of the photosensitive optoelectronic devices of the invention.

DETAILED DESCRIPTION

Figure 1:
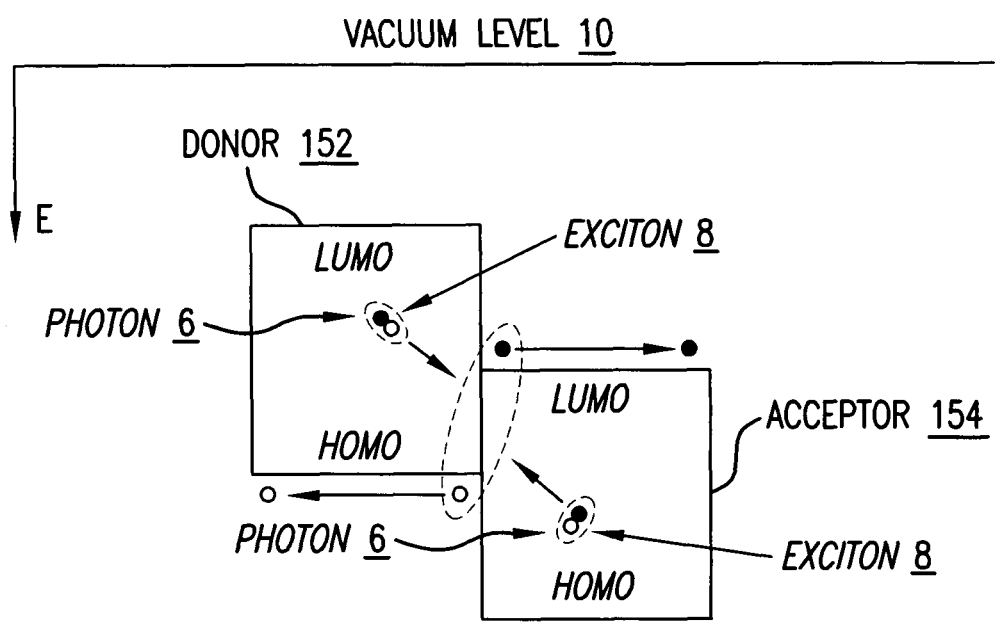
FIG. 1 is an energy level diagram illustrating a donor-acceptor heterojunction.

The nonplanar porphyrins described herein may have applications in optoelectronic devices other than organic solar cells. For example, other optoelectronic devices such as organic photodetectors, organic photosensors, organic photoconductors, chemical sensors and biological sensors may employ the nonplanar porphyrins.

As used herein, photosensitive optoelectronic devices can be solar cells.

As used herein, photosensitive optoelectronic devices can be photodetectors.

As used herein, photosensitive optoelectronic devices can be photosensors.

As used herein, photosensitive optoelectronic devices can be photoconductors.

As used herein, photosensitive optoelectronic devices can be chemical sensors.

As used herein, photosensitive optoelectronic devices can be biological sensors.

As used herein, the term "organic" includes polymeric materials as well as small molecule organic materials that may be used to fabricate organic photosensitive optoelectronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule." In general, a small molecule has a defined chemical formula with a molecular weight that is the same from molecule to molecule, whereas a polymer has a defined chemical formula with a molecular weight that may vary from molecule to molecule. As used herein, "organic" includes metal complexes of hydrocarbyl and heteroatom-substituted hydrocarbyl ligands.

As used herein, "carbocyclic group" means a cyclic chemical group wherein all the ring atoms are carbon. The "carbocyclic group" is monocyclic or multicyclic. The "carbocyclic group" can be a cycloalkyl group, cycloalkenyl group, cycloalkynyl group and aryl group.

As used herein, "heterocyclic group" refers to a cyclic chemical group having at least one N, O or S ring atom, with C atom(s) as the remaining ring atom(s). The "heterocyclic group" is monocyclic or multicyclic. When the "heterocyclic group" is aromatic, it is called a "heteroaryl group." The heterocyclic group can be a cyclic group comprising a 4-, 5-, 6-, 7- or 8-membered ring, wherein the ring comprises at least one ring atom selected from the group consisting of N, O and S with C as the remaining ring atom(s). Examples of the heterocyclic group include pyrrolidinyl group, piperidinyl group, piperazinyl group, morpholino group, thiomorpholino group, homopiperidinyl group, chromanyl group, isochromanyl group, chromenyl group, pyrrolyl group, furanyl group, thienyl group, pyrazolyl group, imidazolyl group, furazanyl group, oxazolyl group, isoxazolyl group, thiazolyl group, isothiazolyl group, pyridyl group, pyridazinyl group, pyrimidinyl group, pyrazinyl group, pyranyl group, indolyl group, isoindolyl group, indazolyl group, purinyl group, indolizinyl group, quinolinyl group, isoquinolinyl group, quinazolinyl group, pteridinyl group, quinolizinyl group, benzoxazinyl group, carbazolyl group, phenazinyl group, phenothiazinyl group and phenanthridinyl group.

As used herein, when the term "monocyclic" is used to modify "carbocyclic group" or "heterocyclic group", the carbocyclic group or heterocyclic group comprises only a single ring.

As used herein, when the term "multicyclic" is used to modify "carbocyclic group" or "heterocyclic group", the carbocyclic group or heterocyclic group comprises at least two rings. Examples of "multicyclic" include bicyclic, tricyclic and tetracyclic. Some or all of the rings in the "multicyclic" group can be peri-fused, ortho-fused and/or bridged. The "multicyclic" group can be a spiro group.

As used herein, a "valence atom" of a chemical group refers to the atom of the chemical group that attaches to another chemical group or atom.

As used herein, the term "hydrocarbyl group" refers to a chemical group having carbon and hydrogen atoms.

As used herein, the term "alkyl group" means a straight-chain or branched saturated hydrocarbyl group. Preferably, the "alkyl group" is $C_1$-$C_6$. Examples of the alkyl group include methyl, ethyl, n-propyl, isopropyl, n-butyl, sec-butyl, isobutyl, tert-butyl, n-pentyl and n-hexyl.

As used hereon, the term "alkenyl group" means a hydrocarbyl group comprising at least one C=C double bond. Preferably, the "alkenyl group" is $C_2$-$C_6$. An example of the alkenyl group is vinyl.

As used herein, the term "alkynyl group" means a hydrocarbyl group comprising at least one carbon-to-carbon triple bond. The term "alkynyl group" includes a chemical group having at least one carbon-to-carbon triple bond and at least one C=C double bond. Preferably, the "alkynyl group" is $C_2$-$C_6$.

As used herein, the term "cycloalkyl group" means a saturated cyclic hydrocarbyl group. The "cycloalkyl group" is monocyclic or multicyclic. The "cycloalkyl group" can be $C_3$-$C_8$. Examples of "cycloalkyl group" include cyclobutyl, cyclopentyl, cyclohexyl, cycloheptyl, cyclooctyl and cyclononyl.

As used herein, the term "cycloalkenyl group" means an unsaturated cyclic hydrocarbyl group having at least one C=C double bond. The "cycloalkenyl group" is monocyclic or multicyclic. The "cycloalkenyl group" can be $C_3$-$C_8$.

As used herein, the term "cycloalkynyl group" means an unsaturated cyclic hydrocarbyl group having at least one carbon-to-carbon triple bond. The "cycloalkynyl group" is monocyclic or multicyclic. The "cycloalkynyl group" can be $C_3$-$C_8$.

As used herein, the term "aryl group" means an aromatic hydrocarbyl group. The "aryl group" is monocyclic or multicyclic. The "aryl group" can be $C_6$-$C_{10}$. Examples of the "aryl group" include phenyl group and naphthyl group.

As used herein, the term "aralkyl group" refers to an alkyl group substituted with at least one aryl group. The aryl portion of the "aralkyl group" can be $C_6$-$C_{10}$. The alkyl portion of the "aralkyl group" can be $C_1$-$C_6$. Example of the "aralkyl group" are benzyl group, i.e., phenylmethyl group, and 2-phenylethyl group.

As used herein, when a chemical group is modified by "substituted" that means the chemical group has at least one hydrogen atom replaced by a substituent. Examples of the substituent include a radical selected from the group consisting of alkyl groups, alkenyl groups, alkynyl groups, cycloalkyl groups, cycloalkenyl groups, cycloalkynyl groups, aryl groups, heterocyclic groups, hydroxy group, alkoxy groups, alkenyloxy groups, alkynyloxy groups, cycloalkoxy groups, cycloalkenyloxy groups, cycloalkynyloxy groups, aryloxy groups, alkylcarbonyloxy groups, cycloalkylcarbonyloxy groups, cycloalkenylcarbonyloxy groups, cycloalkynylcarbonyloxy groups, arylcarbonyloxy groups, thiol group, alkylthio groups, cycloalkylthio groups, cycloalkenylthio groups, cycloalkynylthio groups, arylthio groups, formyl group, acyl groups, carbamoyl groups, amino group, amino groups substituted with at least one alkyl group, alkenyl group or alkynyl group, acylamino groups, N-acyl-N-alkyl amino groups, N-acyl-N-alkenyl amino groups, N-acyl-N-alkynyl amino groups, N-acyl-N-cycloalkyl amino groups, N-acyl-N-cycloalkenyl amino groups, N-acyl-N-aryl amino groups, nitro group, heterocyclic groups and halogen atoms.

Examples of a substituted alkyl group include an aralkyl group, cycloalkyl substituted alkyl group, cycloalkenyl substituted alkyl group, hydroxyl substituted alkyl group, alkoxy substituted alkyl group, cycloalkoxy substituted alkyl group, aryloxy substituted alkyl group, alkylcarbonyloxy substituted alkyl group, cycloalkylcarbonyloxy substituted alkyl group, cycloalkenylcarbonyloxy substituted alkyl group, cycloalkynylcarbonyloxy substituted alkyl group, arylcarbonyloxy substituted alkyl group, thiol substituted alkyl group, alkylthio substituted alkyl group, cycloalkylthio substituted alkyl group, formyl substituted alkyl group, acylated alkyl group, carbamoyl substituted alkyl group, amino substituted alkyl group, acylamino substituted alkyl group, nitro substituted alkyl group, halogen substituted alkyl group and heterocyclyl substituted alkyl group.

Examples of a substituted alkenyl group include an aralkenyl group, cycloalkenyl substituted alkenyl group, cycloalkenyl substituted alkenyl group, hydroxyl substituted alkenyl group, alkoxy substituted alkenyl group, cycloalkoxy substituted alkenyl group, aryloxy substituted alkenyl group, alkylcarbonyloxy substituted alkenyl group, cycloalkylcarbonyloxy substituted alkenyl group, cycloalkenylcarbonyloxy substituted alkenyl group, cycloalkynylcarbonyloxy substituted alkenyl group, arylcarbonyloxy substituted alkenyl group, thiol substituted alkenyl group, alkylthio substituted alkenyl group, cycloalkylthio substituted alkenyl group, formyl substituted alkenyl group, acylated alkenyl group, carbamoyl substituted alkenyl group, amino substituted alkenyl group, acylamino substituted alkenyl group, nitro substituted alkenyl group, halogen substituted alkenyl group and heterocyclyl substituted alkenyl group.

Examples of a substituted alkynyl group include an aralkynyl group, cycloalkyl substituted alkynyl group, cycloalkenyl substituted alkynyl group, hydroxyl substituted alkynyl group, alkoxy substituted alkynyl group, cycloalkoxy substituted alkynyl group, aryloxy substituted alkynyl group, alkylcarbonyloxy substituted alkynyl group, cycloalkylcarbonyloxy substituted alkynyl group, cycloalkenylcarbonyloxy substituted alkynyl group, cycloalkynylcarbonyloxy substituted alkynyl group, arylcarbonyloxy substituted alkynyl group, thiol substituted alkynyl group, alkylthio substituted alkynyl group, cycloalkylthio substituted alkynyl group, formyl substituted alkynyl group, acylated alkynyl group, carbamoyl substituted alkynyl group, amino substituted alkynyl group, acylamino substituted alkynyl group, nitro substituted alkynyl group, halogen substituted alkynyl group and heterocyclyl substituted alkynyl group.

Examples of a substituted cycloalkyl group include an alkyl substituted cycloalkyl group, aryl substituted cycloalkyl group, cycloalkyl substituted cycloalkyl group, cycloalkenyl substituted cycloalkyl group, cycloalkynyl substituted cycloalkyl group, hydroxyl substituted cycloalkyl group, alkoxy substituted cycloalkyl group, cycloalkoxy substituted cycloalkyl group, aryloxy substituted cycloalkyl group, alkylcarbonyloxy substituted cycloalkyl group, cycloalkylcarbonyloxy substituted cycloalkyl group, cycloalkenylcarbonyloxy substituted cycloalkyl group, cycloalkynylcarbonyloxy substituted cycloalkyl group, arylcarbonyloxy substituted cycloalkyl group, thiol substituted cycloalkyl group, alkylthio substituted cycloalkyl group, cycloalkylthio substituted cycloalkyl group, formyl substituted cycloalkyl group, acylated cycloalkyl group, carbamoyl substituted cycloalkyl group, amino substituted cycloalkyl group, acylamino substituted cycloalkyl group, nitro substituted cycloalkyl group, halogen substituted cycloalkyl group and heterocyclyl substituted cycloalkyl group.

Examples of a substituted cycloalkenyl group include an alkyl substituted cycloalkenyl group, aryl substituted cycloalkenyl group, cycloalkyl substituted cycloalkenyl group, cycloalkenyl substituted cycloalkenyl group, cycloalkynyl substituted cycloalkenyl group, hydroxyl substituted cycloalkenyl group, alkoxy substituted cycloalkenyl group, cycloalkoxy substituted cycloalkenyl group, aryloxy substituted cycloalkenyl group, alkylcarbonyloxy substituted cycloalkenyl group, cycloalkylcarbonyloxy substituted cycloalkenyl group, cycloalkenylcarbonyloxy substituted cycloalkenyl group, cycloalkynylcarbonyloxy substituted cycloalkenyl group, arylcarbonyloxy substituted cycloalkenyl group, thiol substituted cycloalkenyl group, alkylthio substituted cycloalkenyl group, cycloalkylthio substituted cycloalkenyl group, formyl substituted cycloalkenyl group, acylated cycloalkenyl group, carbamoyl substituted cycloalkenyl group, amino substituted cycloalkenyl group, acylamino substituted cycloalkenyl group, nitro substituted cycloalkenyl group, halogen substituted cycloalkenyl group and heterocyclyl substituted cycloalkenyl group.

Examples of a substituted cycloalkynyl group include an alkyl substituted cycloalkynyl group, aryl substituted cycloalkynyl group, cycloalkyl substituted cycloalkynyl group, cycloalkenyl substituted cycloalkynyl group, cycloalkynyl substituted cycloalkynyl group, hydroxyl substituted cycloalkynyl group, alkoxy substituted cycloalkynyl group, cycloalkoxy substituted cycloalkynyl group, aryloxy substituted cycloalkynyl group, alkylcarbonyloxy substituted cycloalkynyl group, cycloalkylcarbonyloxy substituted cycloalkynyl group, cycloalkenylcarbonyloxy substituted cycloalkynyl group, cycloalkynylcarbonyloxy substituted cycloalkynyl group, arylcarbonyloxy substituted cycloalkynyl group, thiol substituted cycloalkynyl group, alkylthio substituted cycloalkynyl group, cycloalkylthio substituted cycloalkynyl group, formyl substituted cycloalkynyl group, acylated cycloalkynyl group, carbamoyl substituted cycloalkynyl group, amino substituted cycloalkynyl group, acylamino substituted cycloalkynyl group, nitro substituted cycloalkynyl group, halogen substituted cycloalkynyl group and heterocyclyl substituted cycloalkynyl group.

Examples of a substituted aryl group include an alkyl substituted aryl group, aryl substituted aryl group, cycloalkyl substituted aryl group, cycloalkenyl substituted aryl group, cycloalkynyl substituted aryl group, hydroxyl substituted aryl group, alkoxy substituted aryl group, cycloalkoxy substituted aryl group, aryloxy substituted aryl group, alkylcarbonyloxy substituted aryl group, cycloalkylcarbonyloxy substituted aryl group, cycloalkenylcarbonyloxy substituted aryl group, cycloalkynylcarbonyloxy substituted aryl group, arylcarbonyloxy substituted aryl group, thiol substituted aryl group, alkylthio substituted aryl group, cycloalkylthio substituted aryl group, formyl substituted aryl group, acylated aryl group, carbamoyl substituted aryl group, amino substituted aryl group, acylamino substituted aryl group, nitro substituted aryl group, halogen substituted aryl group and heterocyclyl substituted aryl group.

Examples of a substituted heterocyclic group include an alkyl substituted heterocyclic group, aryl substituted heterocyclic group, cycloalkyl substituted heterocyclic group, cycloalkenyl substituted heterocyclic group, cycloalkynyl substituted heterocyclic group, hydroxyl substituted heterocyclic group, alkoxy substituted heterocyclic group, cycloalkoxy substituted heterocyclic group, aryloxy substituted heterocyclic group, alkylcarbonyloxy substituted heterocyclic group, cycloalkylcarbonyloxy substituted heterocyclic group, cycloalkenylcarbonyloxy substituted heterocyclic group, cycloalkynylcarbonyloxy substituted heterocyclic group, arylcarbonyloxy substituted heterocyclic group, thiol substituted heterocyclic group, alkylthio substituted heterocyclic group, cycloalkylthio substituted heterocyclic group, formyl substituted heterocyclic group, acylated heterocyclic group, carbamoyl substituted heterocyclic group, amino substituted heterocyclic group, acylamino substituted heterocyclic group, nitro substituted heterocyclic group, halogen substituted heterocyclic group and heterocyclyl substituted heterocyclic group.

In some of the embodiments of the photosensitive optoelectronic device of the present invention, the valence atom in at least one R or R' group is a carbon atom.

In some of the embodiments of the photosensitive optoelectronic device of the present invention, the valence atom in at least one R or R' group is a carbon atom, wherein the at least one R' or R group is independently selected from the group consisting of alkyl group, substituted alkyl group, alkenyl group, substituted alkenyl group, alkynyl group, substituted alkynyl group, cycloalkyl group, substituted cycloalkyl group, cycloalkenyl group, substituted cycloalkenyl group, cycloalkynyl group, substituted cycloalkynyl group, aryl group, substituted aryl group, heterocyclic group and substituted heterocyclic group.

In some of the embodiments of the photosensitive optoelectronic device of the present invention, the valence atom in at least one R or R' group is a carbon atom, wherein the at least one R' or R group is independently selected from the group consisting of alkyl groups, alkenyl groups, alkynyl groups, cycloalkyl groups, cycloalkenyl groups, cycloalkynyl groups, aryl groups and heterocyclic groups.

In some of the embodiments of the photosensitive optoelectronic device of the present invention, the valence atom in at least one R or R' group is a carbon atom, wherein the at least one R' or R group is independently selected from the group consisting of alkyl groups, substituted alkyl groups, aryl groups or substituted aryl groups.

In some of the embodiments of the photosensitive optoelectronic device of the present invention, the valence atom in at least one R or R' group is a carbon atom, wherein the at least one R' or R group is independently selected from the group consisting of phenyl group, tolyl group, xylyl group, mesityl group, methyl group, ethyl group, n-propyl group and isopropyl group.

In some of the embodiments of the photosensitive optoelectronic device of the present invention, the valence atoms of two adjacent R groups of at least one pyrrole ring are carbon atoms, and wherein the two adjacent R groups of the at least one pyrrole ring together with the two β carbon atoms of the at least one pyrrole ring form a carbocyclic group or substituted carbocyclic group.

In some of the embodiments of the photosensitive optoelectronic device of the present invention, the valence atoms of two adjacent R groups of at least one pyrrole ring are carbon atoms, and wherein the two adjacent R groups of the at least one pyrrole ring together with the two β carbon atoms of the at least one pyrrole ring form a heterocyclic group or substituted heterocyclic group.

In some of the embodiments of the photosensitive optoelectronic device of the present invention, the valence atoms of two adjacent R groups of at least one pyrrole ring are carbon atoms, wherein the two adjacent R groups of the at least one pyrrole ring together with the two β carbon atoms of the at least one pyrrole ring form a carbocyclic group or substituted carbocyclic group, and the carbocyclic group or substituted carbocyclic group is a macrocycle or benzanulated π-system.

In some of the embodiments of the photosensitive optoelectronic device of the present invention, the valence atoms of two adjacent R groups of at least one pyrrole ring are carbon atoms, wherein the two adjacent R groups of the at least one pyrrole ring together with the two β carbon atoms of the at least one pyrrole ring form a carbocyclic group or substituted carbocyclic group, and the carbocyclic group or substituted carbocyclic group is aromatic.

In some of the embodiments of the photosensitive optoelectronic device of the present invention, two adjacent R groups of at least one pyrrole ring together with the two β carbon atoms of the at least one pyrrole ring form a heterocyclic group or substituted heterocyclic group.

Figure 10:
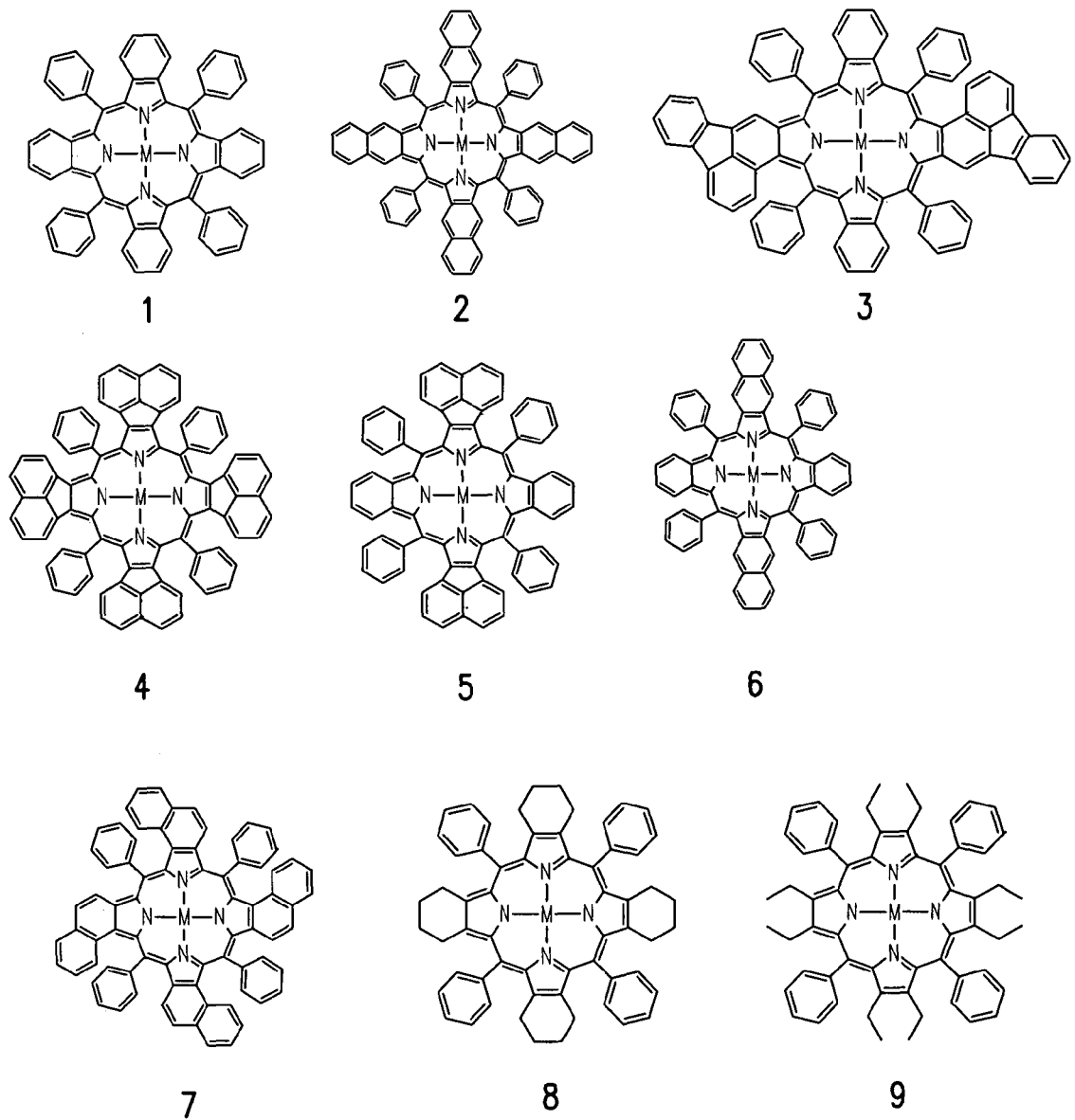
FIG. 10 shows examples of tetraphenyl porphyrin with modified π-system size of the pyrrole unit.

In some of the embodiments of the photosensitive optoelectronic device of the present invention, the at least one nonplanar porphyrin of formula (I) is selected from the compounds having one of the formulae presented in FIG. 10.

In some of the embodiments of the photosensitive optoelectronic device of the present invention, the valence atom in at least one R or R' group is an oxygen atom.

In some of the embodiments of the photosensitive optoelectronic device of the present invention, the valence atom in at least one R or R' group is an oxygen atom, wherein the at least one R' or R group having O as the valence atom is hydroxy, alkoxy, alkenyloxy, alkynyloxy, cycloakoxy, cycloalkenyloxy, cycloalknyloxy, aralkyloxy, aralkenyloxy, aralkynyloxy, aryloxy, alkylcarbonyloxy, alkenylcarbonyloxy, alkynylcarbonyloxy, hydroxycarbonyloxy or alkoxycarbonyloxy.

In some of the embodiments of the photosensitive optoelectronic device of the present invention, the valence atom in at least one R or R' group is an oxygen atom, wherein the at least one R' or R group having O as the valence atom is hydroxy or alkoxy.

In some of the embodiments of the photosensitive optoelectronic device of the present invention, the valence atom in at least one R or R' group is an oxygen atom, wherein the at least one R' or R group having O as the valence atom is hydroxy, methoxy, ethoxy, n-propoxy or isopropoxy.

In some of the embodiments of the photosensitive optoelectronic device of the present invention, at least one R or R' group is a Cl atom, Br atom, I atom or At atom.

In some of the embodiments of the photosensitive optoelectronic device of the present invention, the valence atom in at least one R or R' group is a nitrogen atom.

In some of the embodiments of the photosensitive optoelectronic device of the present invention, the valence atom in at least one R or R' group is a nitrogen atom, wherein the at least one R or R' group having N as the valence atom is selected from the group consisting of amino group, alkylamino groups, dialkylamino groups, alkenylamino groups, dialkenylamino groups, alkynylamino groups, dialkynylamino groups, N-alkyl-N-alkenylamino groups, N-alkyl-N-alkynylamino groups, N-alkenyl-N-alkynylamino groups, acylamino groups, N-acyl-N-alkyl amino groups, N-acyl-N-alkenyl amino groups, N-acyl-N-alkynyl amino groups, N-acyl-N-cycloalkyl amino groups, N-acyl-N-cycloalkenyl amino groups, N-acyl-N-aryl amino groups, nitro group, heterocyclic groups comprising a nitrogen valence atom and substituted heterocyclic groups comprising a nitrogen valence atom.

In some of the embodiments of the photosensitive optoelectronic device of the present invention, the valence atom in at least one R or R' group is a sulfur atom.

In some of the embodiments of the photosensitive optoelectronic device of the present invention, the valence atom in at least one R or R' group is a sulfur atom, wherein the at least one R or R' group is selected from the group consisting of thiol group, alkylthio groups, alkenylthio groups, alkynylthio groups, aralkylthio groups, aralkenyltho groups, aralkynylthio groups, cycloalkylalkylthio groups, cycloalkenylalkylthio groups, cycloalkynylalkylthio groups, cycloalkylthio groups, cycloalkenylthio groups, cycloalkynylthio groups, and arylthio groups.

In some of the embodiments of the photosensitive optoelectronic device of the present invention, M is Pt, Pd or Ir. Preferably, M is Pt or Pd. More preferably, M is Pt.

In some of the embodiments of the photosensitive optoelectronic device of the present invention, at least one nonplanar porphyrin is Pt(tetraphenyl benzo-porphyrin).

In some of the embodiments of the photosensitive optoelectronic device of the present invention, at least one nonplanar porphyrin is Pd(tetraphenyl benzo-porphyrin).

In some of the embodiments of the photosensitive optoelectronic device of the present invention, the device is an organic photovoltaic cell.

In some of the embodiments of the photosensitive optoelectronic device of the present invention, the device is a photoconductor cell.

In some of the embodiments of the photosensitive optoelectronic device of the present invention, the device is a photosensor.

In some of the embodiments of the photosensitive optoelectronic device of the present invention, the device is a photodetector.

In some of the embodiments of the photosensitive optoelectronic device of the present invention, the device is a chemical sensor.

In some of the embodiments of the photosensitive optoelectronic device of the present invention, the device is a biological sensor.

In some of the embodiments of the photosensitive optoelectronic device of the present invention, the device comprises a donor material and an acceptor material, and wherein the donor material or the acceptor material comprises the at least one nonplanar porphyrin of formula (I).

In some of the embodiments of the photosensitive optoelectronic device of the present invention, the device comprises a donor material and an acceptor material, and wherein both the donor material and the acceptor material comprises at least one nonplanar porphyrin of formula (I), the at least one nonplanar porphyrin in the donor material is different from the at least one nonplanar porphyrin in the acceptor material.

In some of the embodiments of the photosensitive optoelectronic device of the present invention, the device comprises a donor material and an acceptor material, and wherein the donor material comprises the at least one nonplanar porphyrin of formula (I), and the acceptor material comprises a $C_{60}$ compound.

The present invention provides a method for fabricating the photosensitive optoelectronic device of the present invention, the method comprising providing a donor material and an acceptor material, wherein the donor material and/or the acceptor material comprises at least one nonplanar porphyrin of formula (I) of the present invention; and making the photosenstive optoelectronic device comprising putting the donor material in contact with the acceptor material, wherein when both the donor material and acceptor material comprise at least one nonplanar porphyrin of formula (I), the at least one nonplanar porphyrin in the donor material is different from the at least one nonplanar porphyrin in the acceptor material.

One of the aspects of the invention concerns a method for fabricating the photosensitive optoelectronic device of the present invention, wherein the photosensitive optoelectronic device is fabricated with any known method of making photosensitive optoelectronic devices, the improvement comprising:

providing a donor material and an acceptor material, wherein the donor material and/or the acceptor material comprises at least one nonplanar porphyrin of formula (I) of the present invention; and putting the donor material in contact with the acceptor material, wherein when both the donor material and acceptor material comprise at least one nonplanar porphyrin of formula (I), the at least one nonplanar porphyrin in the donor material is different from the at least one nonplanar porphyrin in the acceptor material.

In any of the methods for fabricating the photosensitive optoelectronic device of the present invention, the at least one nonplanar porphyrin used in the donor material and/or the acceptor material can be any nonplanar porphyrin of formula (I) disclosed herein.

In some of the embodiments of the methods for fabricating the photosensitive optoelectronic device of the present invention, the photosensitive optoelectronic device is a solar cell.

In some of the embodiments of the methods for fabricating the photosensitive optoelectronic device of the present invention, the photosensitive optoelectronic device is a photodetector.

In some of the embodiments of the methods for fabricating the photosensitive optoelectronic device of the present invention, the photosensitive optoelectronic device is a photo sensor.

In some of the embodiments of the methods for fabricating the photosensitive optoelectronic device of the present invention, the photosensitive optoelectronic device is a photoconductor cell.

In some of the embodiments of the methods for fabricating the photosensitive optoelectronic device of the present invention, the photosensitive optoelectronic device is a chemical sensor.

In some of the embodiments of the methods for fabricating the photosensitive optoelectronic device of the present invention, the photosensitive optoelectronic device is a biological sensor.

The nonplanar porphyrin of formula (I) can be prepared with known chemical synthesis methods such as the methods illustrated with the synthetic schemes outlined below.

General Pyrrole Synthesis (Barton-Zard Reaction)

Substituted vinyl nitro compounds may be reacted under nonnucleophilic basic conditions with ethyl isocyano acetate to form carboxyl ester substituted pyrrole derivatives. The carboxyl ester substituted pyrrole derivatives may then be decarboxylated under basic conditions to yield the pyrrolic moiety.

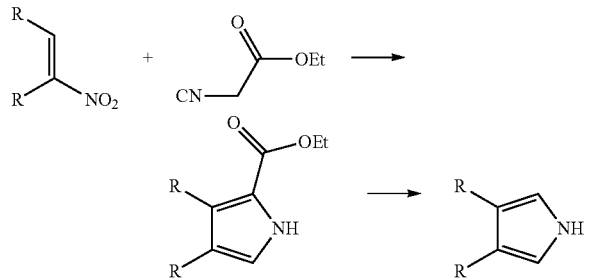

General Porphyrin Synthesis (Compounds 1-9):

Substituted pyrroles are reacted with a substituted aldehyde under Lindsey conditions with subsequent oxidation to form the 2H-porphyrin. Metallation with for example a metal halide yields the metallated porphyrin. M in the reaction scheme below is a metal.

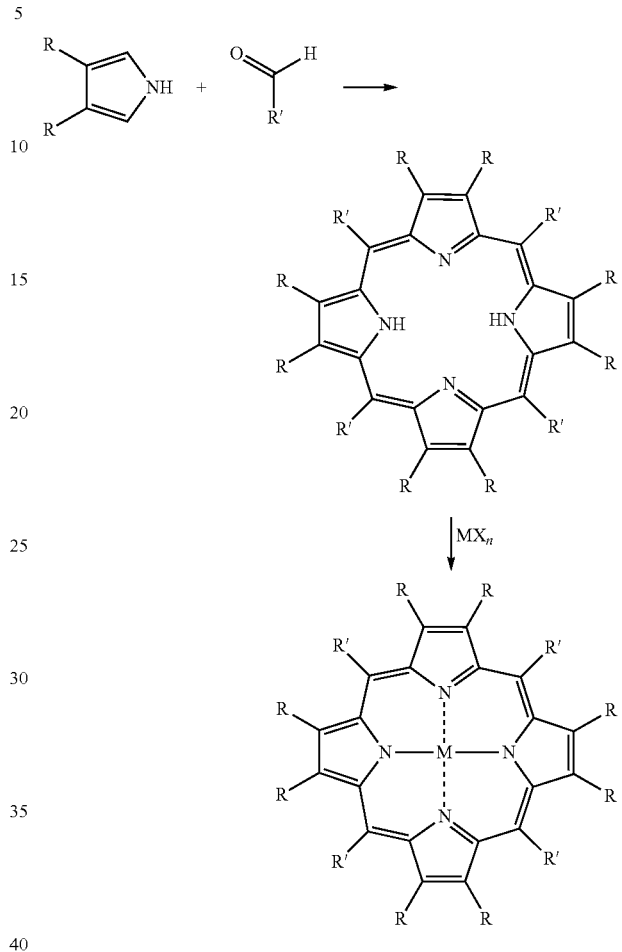

General Synthesis of cis-Substituted Porphyrin:

a) A carboxyl ester protected substituted pyrrole is condensed with a substituted aldehyde to form a dipyrromethane under Lindsey conditions with subsequent decarboxylation under basic conditions.

b) A substituted pyrrole is acylated with benzoyl chloride under Friedel-Crafts conditions and condensed with a substituted aldehyde to form a phenyl ketone substituted dipyrromethane. This phenyl ketone substituted dipyrromethane is reduced with NaBH4 to the corresponding secondary alcohol.

c) The two dipyrromethane moieties prepared in pathways a) and b) are condensed under acidic conditions and oxidized to form a porphyrin and metallated. M in the reaction scheme below is a metal. $R_1$ and $R_2$ are examples of R.

a)

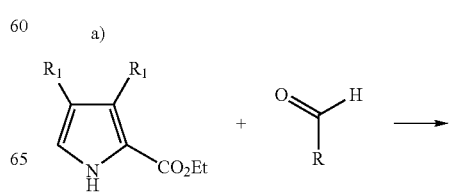

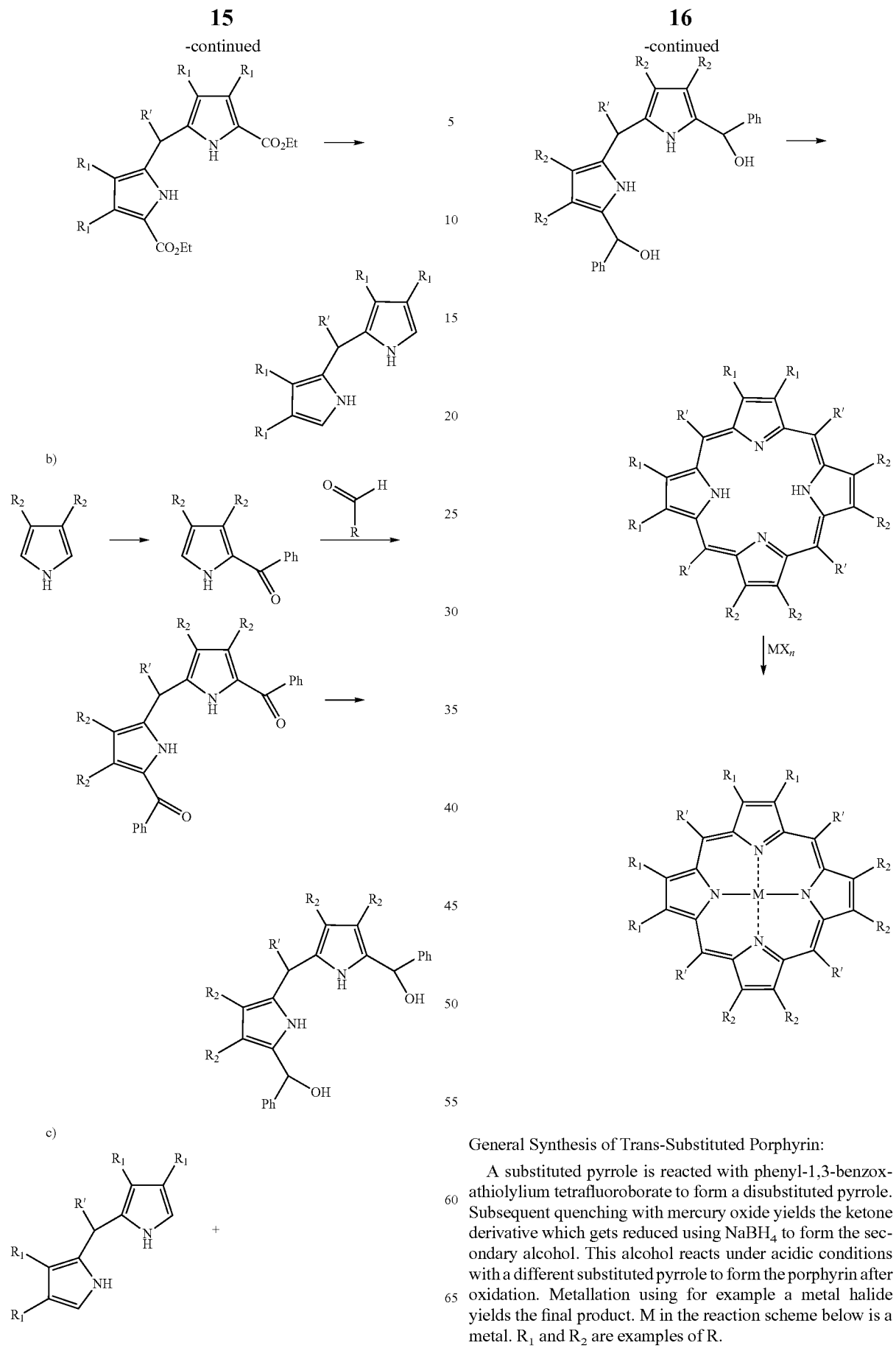

General Synthesis of Trans-Substituted Porphyrin:

A substituted pyrrole is reacted with phenyl-1,3-benzoxathiolylium tetrafluoroborate to form a disubstituted pyrrole. Subsequent quenching with mercury oxide yields the ketone derivative which gets reduced using $NaBH_4$ to form the secondary alcohol. This alcohol reacts under acidic conditions with a different substituted pyrrole to form the porphyrin after oxidation. Metallation using for example a metal halide yields the final product. M in the reaction scheme below is a metal. $R_1$ and $R_2$ are examples of R.

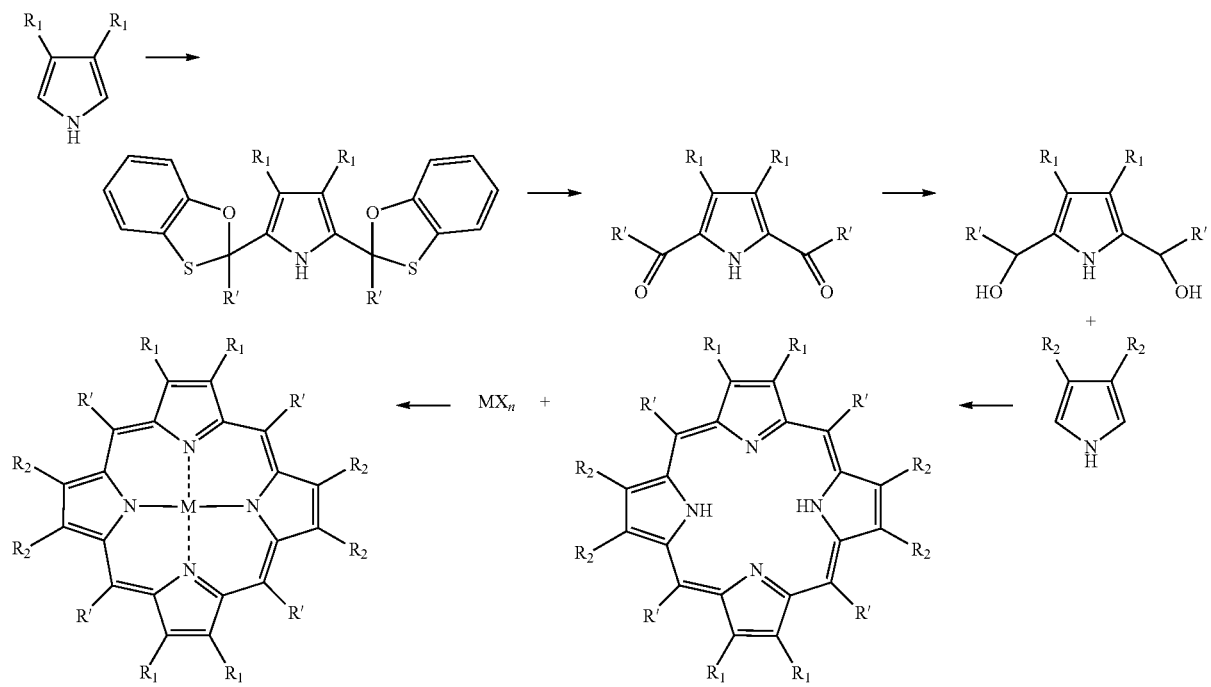

General Synthesis of 3-1-Substituted Porphyrin:

a) A substituted pyrrole is reacted with phenyl-1,3-benzoxathiolylium tetrafluoroborate to form a disubstituted pyrrole. Subsequent quenching with mercury oxide yields a ketone derivative of pyrrole (a bis-2,5-acylated pyrrole), which is reduced using NaBH4 to form a secondary alcohol substituted pyrrole.

b) This secondary alcohol substituted pyrrole is condensed with a substituted carboxylic acid ester protected pyrrole to form a bis-1,3-(pyrrolylmethyl)pyrrole protected with carboxylic ester groups, which are removed under basic conditions in the next step.

c) A differently substituted pyrrole is reacted with phenyl-1,3-benzoxathiolylium tetrafluoroborate to form a disubstituted pyrrole. Subsequent quenching with mercury oxide yields a ketone derivative of pyrrole, which is reduced using NaBH$_4$ to form a secondary alcohol substituted pyrrole.

d) Condensation of the compound prepared in b) and c) under acidic conditions yields the porphyrin after subsequent oxidation. Metallation yields the final porphyrin. M in the reaction scheme below is a metal. $R_1$ and $R_2$ are examples of R.

a)

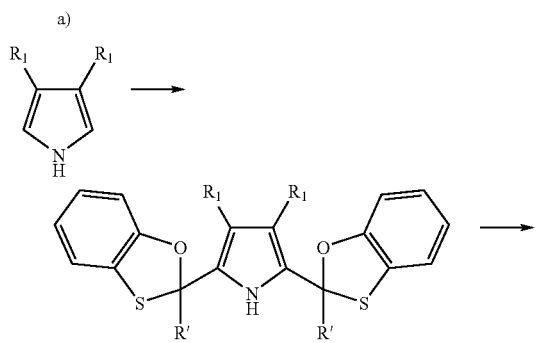

-continued

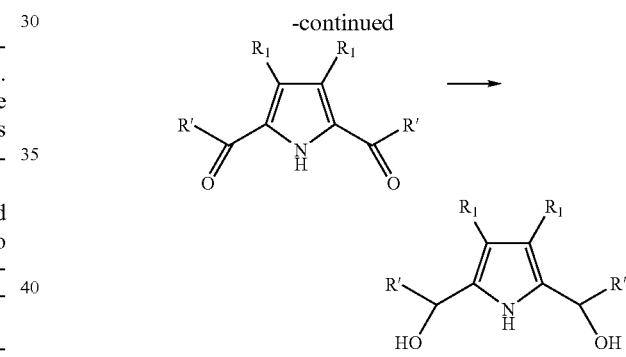

(b)

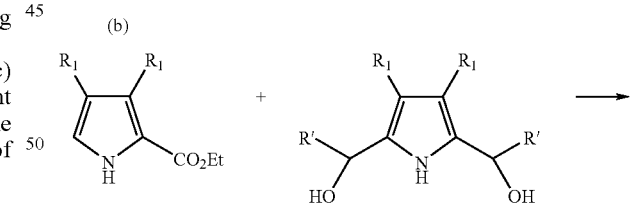

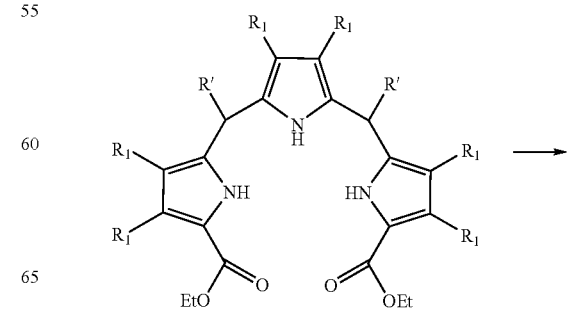

-continued

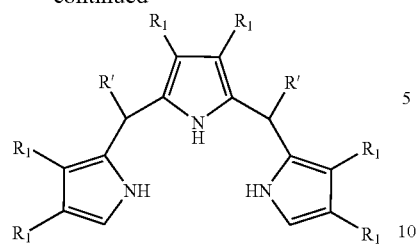

c)
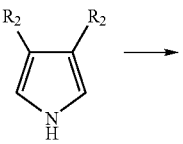

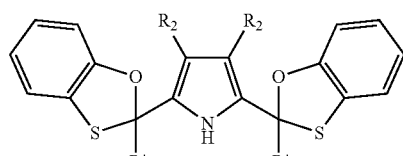

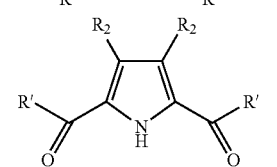

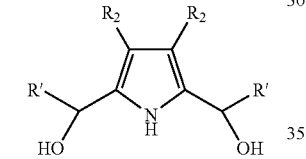

d)
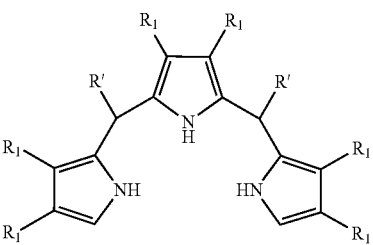    +

-continued

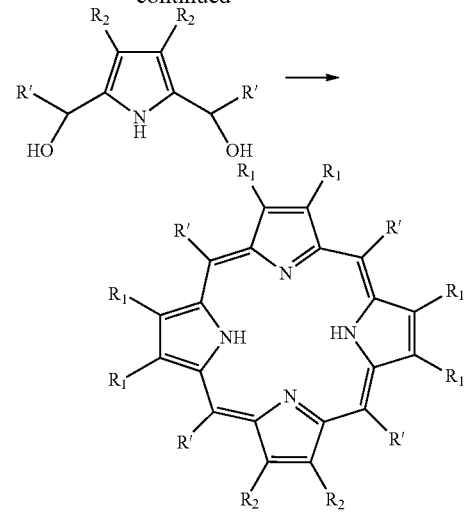

↓ MX$_n$

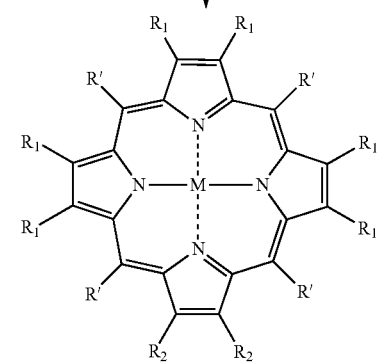

General Synthesis of Br$_8$-Substituted Porphyrin with Further Substitution of the Br:

Pyrrole condensation with a substituted aldehyde under Lindsey conditions yields the porphyrin after oxidation. Subsequent bromination of the porphyrin using, for example, NBS yields the octa-brominated porphyrin. Further reaction at the bromine atoms, for example via Suzuki Coupling, provides access to heteroatom substituted porphyrins. Metallation yields the final product. M in the reaction scheme below is a metal. R$_1$ corresponds to R in formula (I).

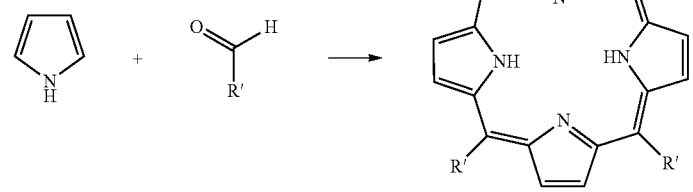

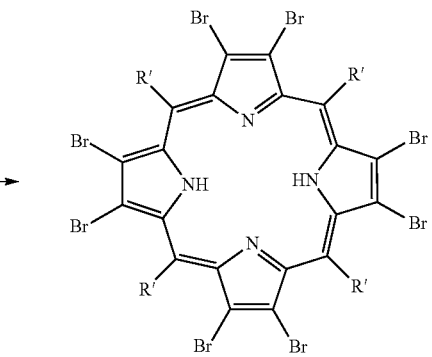

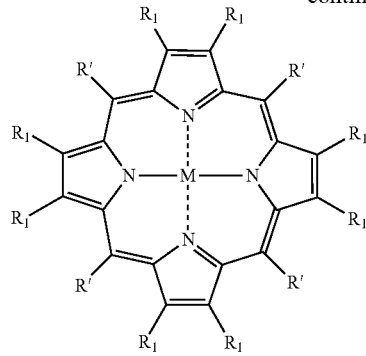
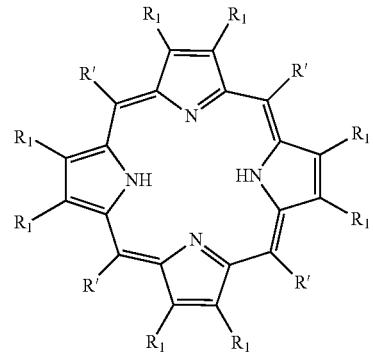

General Synthesis of meso-Br$_4$-Substituted Porphyrin with Further Substitution of the Br:

Pyrrole condensation with dimethyl acetal under acidic conditions yields the porphyrin after oxidation. Subsequent bromination of the porphyrin using, for example, NBS yields the tetra-brominated porphyrin. Further reaction at the bromine atoms, for example via Suzuki coupling, provides access to heteroatom substituted porphyrins. Metallation yields the final product. M in the reaction scheme below is a metal. $R_1$ corresponds to R in formula (I).

tion yielding much more intense bands for the films than any other material used so far for solar applications. This non-broadening and flattening of peaks is assigned to the lack of efficient π-π interaction between neighboring molecules due to the particular non-planarity of the molecule[7].

EXAMPLE

Photovoltaic cells were grown on ITO-coated glass substrates that were solvent cleaned[8] and treated in UV-ozone for

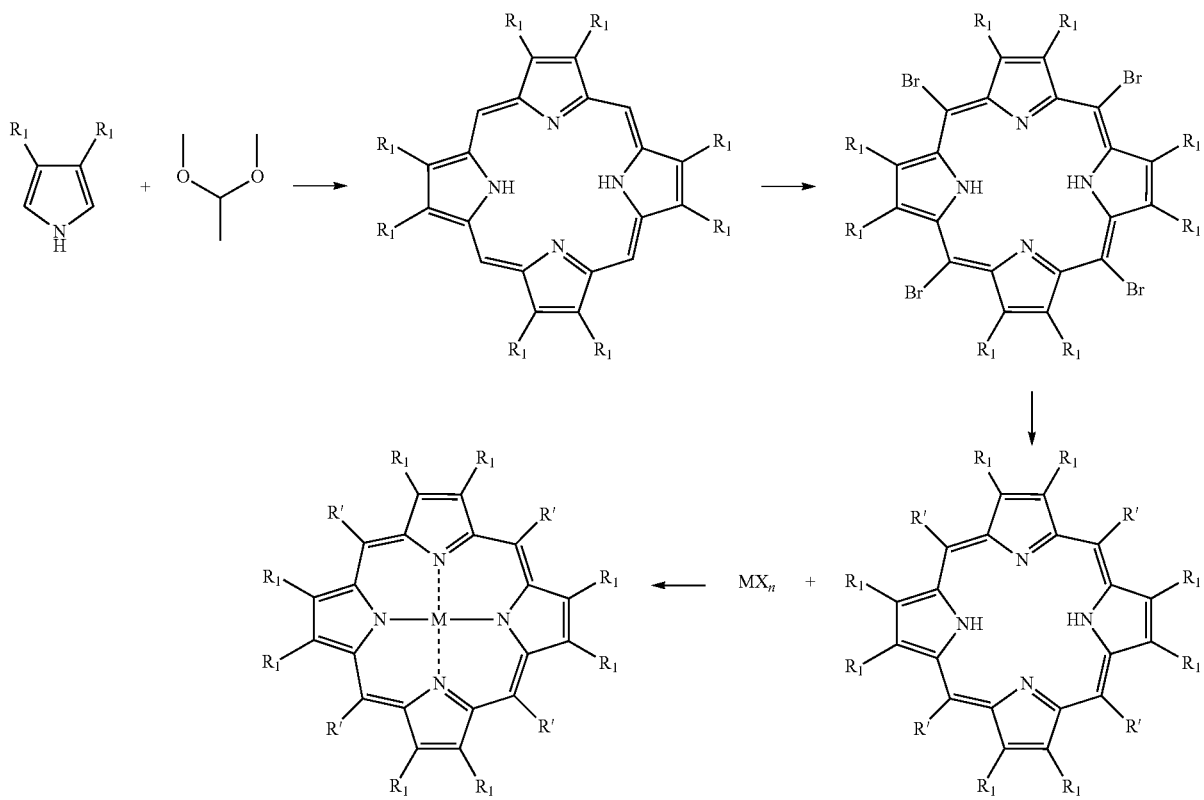

Figure 2:
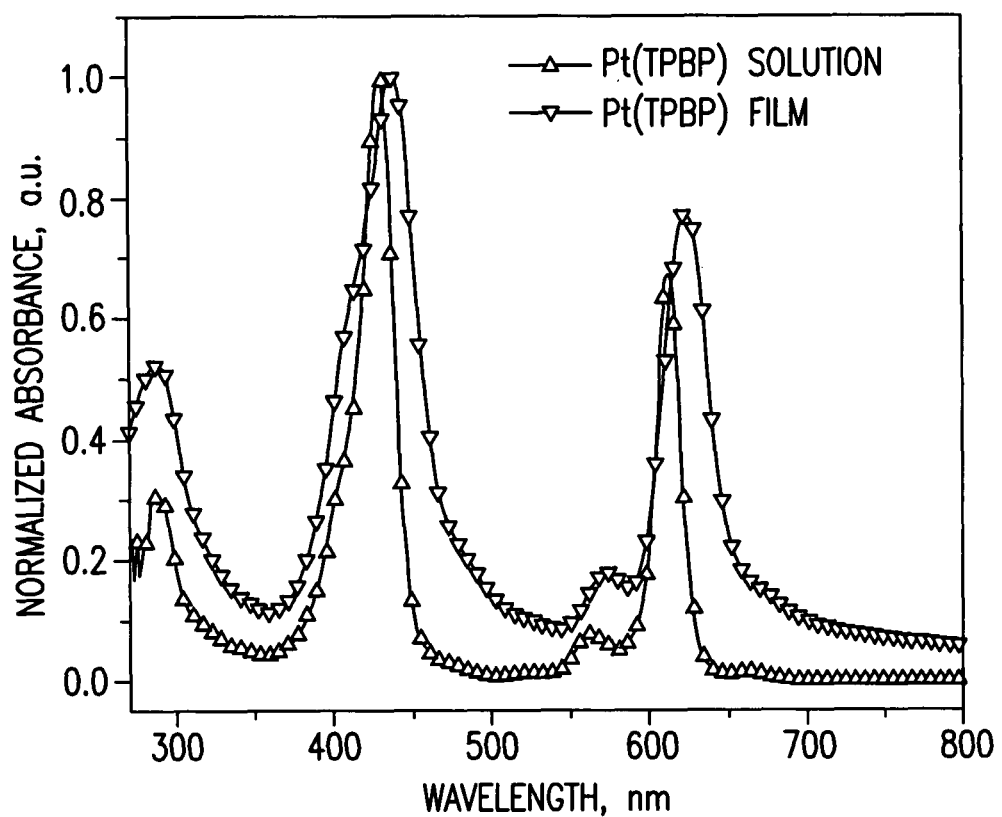
FIG. 2 compares the absorption spectra of Pt(TPBP) dissolved in dichloromethane ("DCM") and a vapor deposited film with the absorptivity normalized for clarity.

A good example of the materials being used in this invention are M(TPBP)s, wherein TPBP stands for tetraphenyl benzoporphyrin. These materials show good absorption spectra for solar cell application. The absorption lies in the visible region of the spectrum with large extinction coefficients (FIG. 2). This very intense absorption is maintained at film forma- 10 minutes immediately prior to loading into a high vacuum (Base pressure ~2×10$^{-6}$ Torr) chamber. The organic materials, M(TPBP) (synthesized in house), CuPc (Aldrich), C$_{60}$ (MTR Limited), and 2,9-dimethyl-4,7-diphenyl-1,10-phenanthroline (BCP) (Aldrich) were purified by sublimation prior to use. Metal cathode materials, Ag and Al (Alfa Aesar)

were used as received. Materials were sequentially grown by vacuum thermal evaporation at the following rates: M(TPBP) (1 Å/sec), $C_{60}$ (2 Å/sec), and 2,9-dimethyl-4,7-diphenyl-1,10-phenanthroline (BCP) (2 Å/sec) and metals: 1000 Å thick Ag (4 Å/sec) or Al (2.5 Å/sec). The cathode was evaporated through a shadow mask with 1 mm diameter openings. For solution processed donor, the layers where spin coated for 40 s at 3000 rpm for a final 100 Å and at 1500 rpm for 150 Å. The substrates where then annealed at 90° C. for 30 mins under rough vacuum. Devices where finished by evaporation of following layer under high vacuum. Current-voltage (J-V) characteristics of PV cells were measured under simulated AM1.5G solar illumination (Oriel Instruments) using a Keithley 2420 3A Source Meter. Neutral density filters were used to vary light intensity that was measured with a calibrated broadband optical power meter.

Donor and acceptor thicknesses were experimentally modified for highest power conversion efficiency yielding an optimized structure of M(TPBP) 150 Å/$C_{60}$ 400 Å/BCP 100 Å with Ag or Al as cathode.

Clearly, the success on finding materials suitable for efficient energy conversion will be firstly determined by the ability of the materials to absorb light. The absorption spectrum of this class of porphyrins presents two very intense peaks ($\epsilon$~105 cm-1M-1) in the visible region that overlaps well with the solar spectra. M(TPBP)s are known to be saddle shaped molecules[7] which introduces spatial properties never explored in the field of solar cells. This particular non-planarity causes a poor $\pi$-$\pi$ stacking of the molecules at film formation hence preventing aggregation. As result, it can be observed an absorption spectrum for the film with no evident broadening and flattening of peaks and therefore with extinction coefficients of the same order as those found for solution (FIG. 2), which is almost one order of magnitude higher than those found for the widely used donor CuPc in small molecule solar cells.

Figure 3:
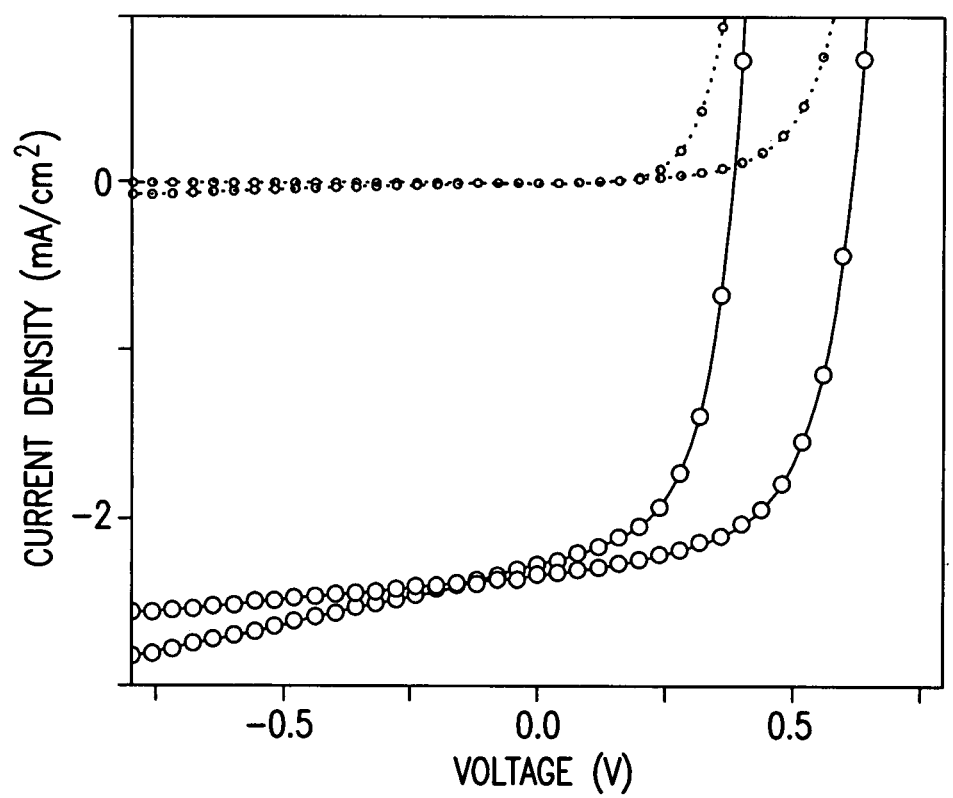
FIG. 3 shows the JV characteristics of ITO/Pt(TPBP)(150 Å)/C$_{60}$(400 Å)/BCP(100 Å)/Al (filled circles) and ITO/CuPc (200 Å)/C60(400 Å)/BCP(100 Å)/Al (open circles) under 1 sun AM 1.5G simulated illumination (solid) and in the dark (dashed).
Figure 4A:
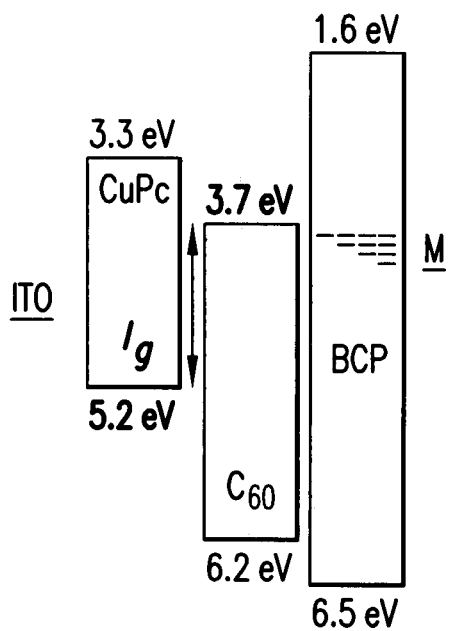
FIG. 4 is a schematic energy level diagram for devices with (a) CuPc or (b) Pt(TPBP) as the donor layer. HOMO energies are from UPS, and the LUMO energies are from IPES measurements, except for Pt(TPBP) where the LUMO and HOMO energies are determined from electrochemistry.
Figure 4B:
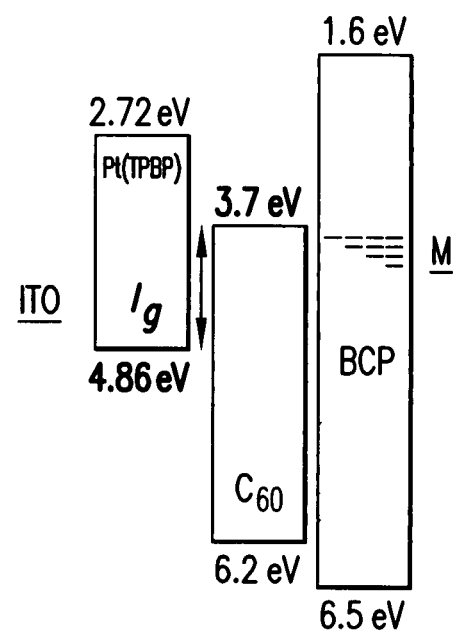

Double heterojunction devices using Pt(TPBP) as the donor-like material and $C_{60}$ as the acceptor material were made using the optimized architecture. Devices perform giving an open circuit voltage larger than that cell considered standard employing CuPc as donor material (FIG. 3). This result generates an interesting discussion since the calculated Ig for the porphyrins system is lower than that of CuPc (FIG. 4). This outcome is opposite to what is expected from the energy level standpoint[5]. However, it is not clear that this relation can be extrapolated and assumed between different systems like porphyrins and phthalocyanines. It is accepted that most of the energy of the photons incident on the cell is not fully utilized and that several losses are occurring within the cell. This result might indicate that the porphyrins system presents more efficient mechanisms for power conversion hence yielding less energy loss and higher power output.

Figure 5:
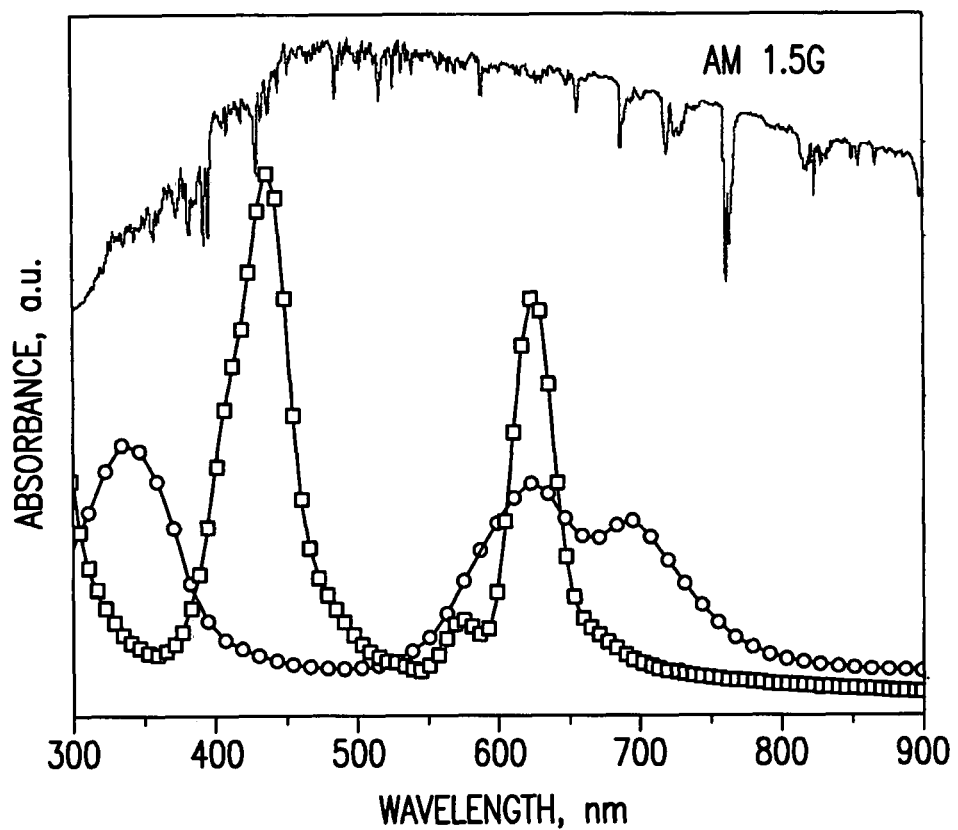
FIG. 5 shows overlapped spectra of a CuPc film (circles) and Pt(TPBP) film (squares). Simulated AM1.5G spectrum, provided by NREL is also shown (line).
Figure 6:
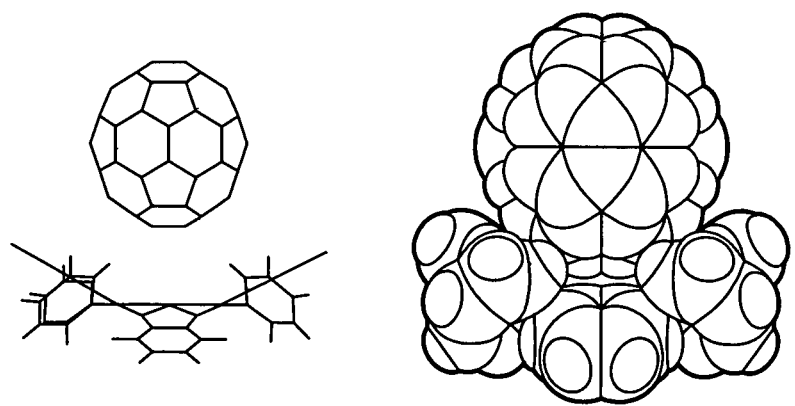
FIG. 6 shows the modeled radius of curvature for C60 and M(TPBP).

Photocurrent on the other hand is not greatly impacted in comparison to the CuPc cell. It is reasonable to think that the amount of light absorbed might be comparable to the standard cell since whatever has been gained in absorptivity for the porphyrin may be comparable to what is gained by a greater spectrum overlap due to broadening of the absorption for CuPc (FIG. 5). The value for the fill factor is somewhat higher than for the standard cell indicating less resistivity to charge flow and good interface contact. It was indicated before that the radius of curvature of the porphyrin matches well that of the $C_{60}$ which would favor a good D/A contact (FIG. 6).

Spin coating of the donor layer yielded devices with poorer performance than those purely vacuum processed. A lower photocurrent can be accounted for by assuming different morphologies resulted from the different layer processing, bearing a less conductive material. The Voc is surprisingly lowered which supports the hypothesis that if losses are high (resistivity, poor interface contact) the argument of energy levels is no longer applicable. In an effort of trying to narrow down the origin of this energy expense, a very thin layer of vapor deposited porphyrin was deposited on top of the solution processed layer. The performance of this cell reproduces very well the pure vapor deposited layer, confirming that the main losses are occurring at the donor/acceptor interface. When the vapor deposited $C_{60}$ is deposited on top of the spin coated Pt(TPBP) the contact is not efficient enough for charge separation hence lowering the Voc and Jsc (FIG. 6).

Figure 7:
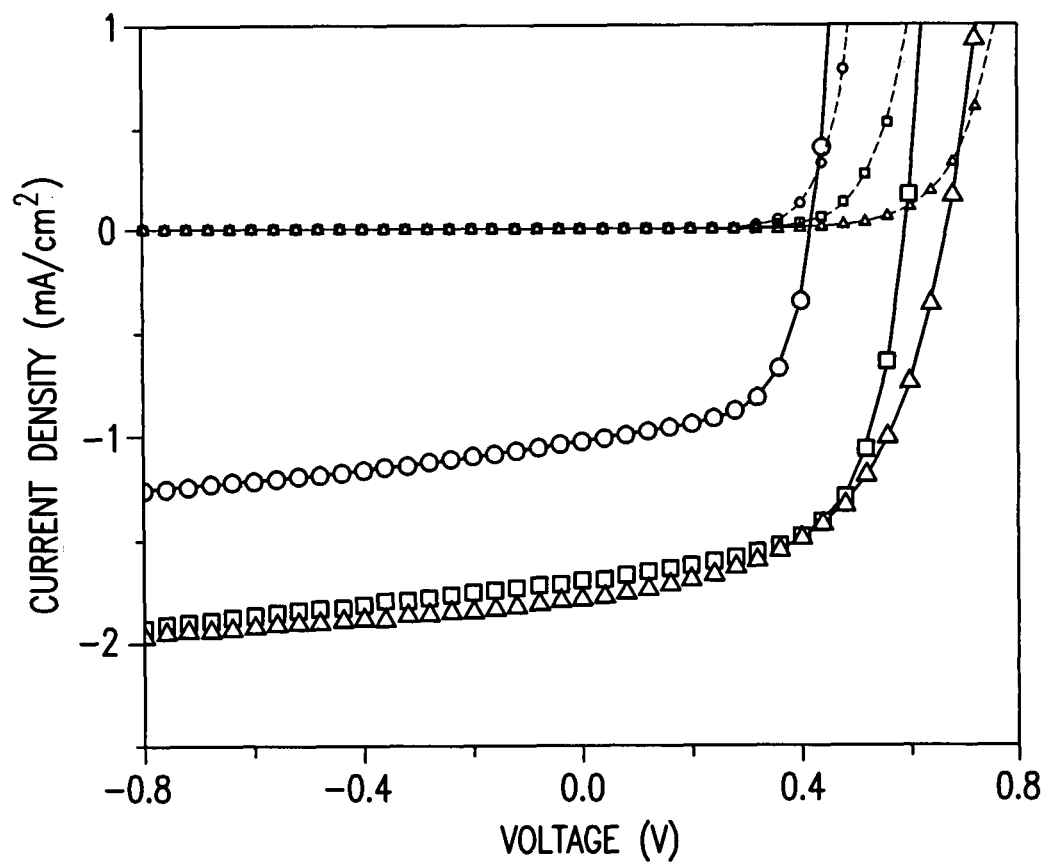
FIG. 7 shows the JV characteristics of ITO/Pt(TPBP)(150 Å)/C$_{60}$(400 Å)/BCP(100 Å)/Al devices. 150 Å of Pt(TPBP) were fully vapor deposited (squares), spin coated (circles) and combination of 100 Å spin coated plus 50 Å vapor deposited on top (triangles).

Additional experiments include the modification of the thickness of the donor layer as depicted in FIG. 7. The efficiency has a maximum at 150 Å with further decline of photocurrent as the thickness is increased. The shapes of the curves remain unchanged with little effect on the FF, which would suggest that the material is transporting charge efficiently even at high thicknesses. It would be expected that if exciton diffusion length is not limiting the amount of excitons reaching the interface then the thicker the layer the more excitons generated and therefore the higher the photocurrent. The trend observed does not clearly correlate with a longer exciton diffusion length but many other factors may be influencing the conversion mechanisms and further experiments that examine exciton diffusion length independently of device fabrication are required to determine this issue.

Figure 8:
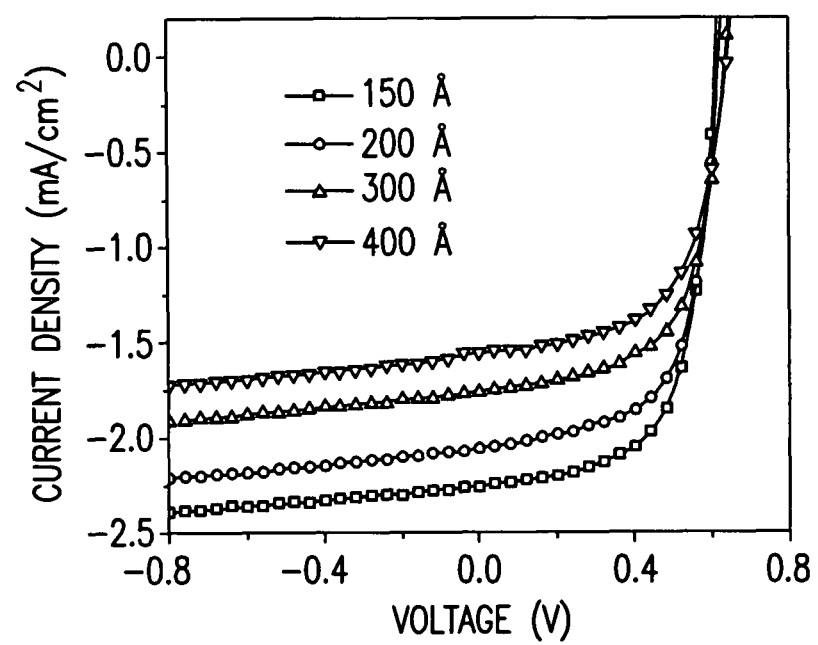
FIG. 8 shows the JV characteristics of ITO/Pt(TPBP)(xÅ)/C$_{60}$(400 Å)/BCP(100 Å)/Al devices.
Figure 9:
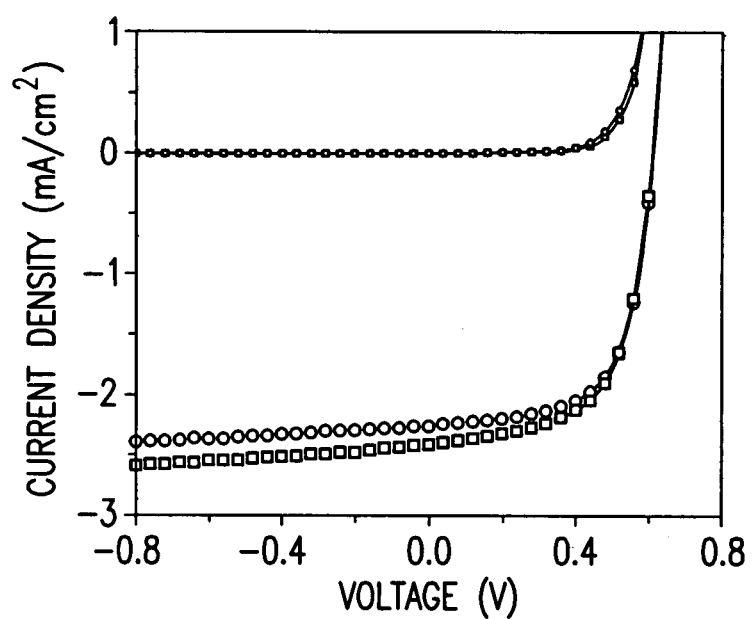
FIG. 9 shows a comparison between Pt(TPBP) and Pd(TPBP) devices in terms of the JV response of ITO/Pt(TPBP) (150 Å)/C$_{60}$(400 Å)/BCP(100 Å)/Al (open circles) and ITO/Pd(TPBP)(150 Å)/C$_{60}$(400 Å)/BCP(100 Å)/Al (squares).

In order to correlate performance of different metallo porphyrins, Pt and Pd tetraphenyl benzo porphyrins were examined (FIG. 8). The performance of both molecules was very comparable which is in agreement with energy levels, absorption spectra and shape of the molecules being so similar. The major difference arises in their triplet lifetime measured in solution, being of 53 µs for the Pt(TPBP), whereas it is almost tripled for the Pd(TPBP) ($\tau_{triplet}$=143 µs). It is worth noting however that these lifetimes were measured in solution, whereas in a film sample there might be considerable self quenching to lower the triplet lifetime to a similar value for both. Thickness dependence of the Pd analog was performed and results mimic those of the Pt porphyrin.

To conclude, the use of metallo tetraphenyl benzo porphyrin yields solar cells with improved performance compared to a standard organic solar cell. It appears that energy losses during charge separation at the donor-acceptor interface are reduced delivering a higher open circuit voltage for lower interface gap energy (Ig). Organic photosensitive optoelectronic devices comprising a wide range of the compounds of formula (I) other than metallo tetraphenyl benzo porphyrin can also achieve better performance than standard organic photosensitive optoelectronic devices. Changing the size of the $\pi$-system of the pyrrole units will shift the emission energy. Replacing the benzo functionality with alkyl groups (comparing formula 1 to formula 8 or 9 in FIG. 10) will maintain the nonplanar nature of the complex, but give a marked blue shift. Extending the $\pi$-system further than that of the benzo functionality will give a marked red shift. There are a large number of compounds that can be envisioned to do this, see formulae 1-9 in FIG. 10, for examples. The nonplanarity of the system can be maintained by having at least one carbon ($CH_3$ as a minimum) at the four meso positions of the porphyrin and to have all of the pyrroles substituted at both positions.

Specific examples of the invention are illustrated and/or described herein. However, it will be appreciated that modifications and variations of the invention are covered by the above teachings and within the purview of the appended claims without departing from the spirit and scope of the invention.

REFERENCES

1. Peumans, P., A. Yakimov, and S. R. Forrest, Small molecular weight organic thin-film photodetectors and solar cells. Journal of Applied Physics, 2003. 93(7): p. 3693-3723.
2. Singh, V. P., R. S. Singh, B. Parthasarathy, A. Aguilera, J. Anthony, and M. Payne, Copper-phthalocyanine-based organic solar cells with high open-circuit voltage. Applied Physics Letters, 2005. 86(8): p. 082106.
3. Brabec, C. J., A. Cravino, D. Meissner, N. S. Sariciftci, T. Fromherz, M. T. Rispens, L. Sanchez, and J. C. Hummelen, Origin of the open circuit voltage of plastic solar cells. Advanced Functional Materials, 2001. 11(5): p. 374-380.
4. Gledhill, S. E., B. Scott, and B. A. Gregg, Organic and nano-structured composite photovoltaics: An overview. Journal of Materials Research, 2005. 20(12): p. 3167-3179.
5. Mutolo, K. L., E. I. Mayo, B. P. Rand, S. R. Forrest, and M. E. Thompson, Enhanced open-circuit voltage in subphthalocyanine/C-60 organic photovoltaic cells. Journal of the American Chemical Society, 2006. 128(25): p. 8108-8109.
6. Terao, Y., H. Sasabe, and C. Adachi, Correlation of hole mobility, exciton diffusion length, and solar cell characteristics in phthalocyanine/fullerene organic solar cells. Applied Physics Letters, 2007. 90(10): p. 103515.
7. Borek, C. K. H., Peter I. Djurovich, Mark E. Thompson, Kristen Aznavour, Robert Bau, Yiru Sun, Stephen R. Forrest, Jason Brooks, Lech Michalski, Julie Brown, Highly Efficient, Near-Infrared Electrophosphorescence from a Pt-Metalloporphyrin Complex. Angewandte Chemie International Edition, 2007. 46(7): p. 1109-1112.
8. Burrows, P. E., Z. Shen, V. Bulovic, D. M. McCarty, S. R. Forrest, J. A. Cronin, and M. E. Thompson, Relationship between electroluminescence and current transport in organic heterojunction light-emitting devices. Journal of Applied Physics, 1996. 79(10): p. 7991-8006.
9. Bredas, J. L., R. Silbey, D. S. Boudreaux, and R. R. Chance, Chain-Length Dependence of Electronic and Electrochemical Properties of Conjugated Systems—Polyacetylene, Polyphenylene, Polythiophene, and Polypyrrole. Journal of the American Chemical Society, 1983. 105(22): p. 6555-6559.
10. D'Andrade, B. W., S. Datta, S. R. Forrest, P. Djurovich, E. Polikarpov, and M. E. Thompson, Relationship between the ionization and oxidation potentials of molecular organic semiconductors. Organic Electronics, 2005. 6(1): p. 11-20.

What is claimed is:

1. An organic photosensitive optoelectronic device comprising a donor material and/or an acceptor material comprising at least one nonplanar porphyrin of formula (I),

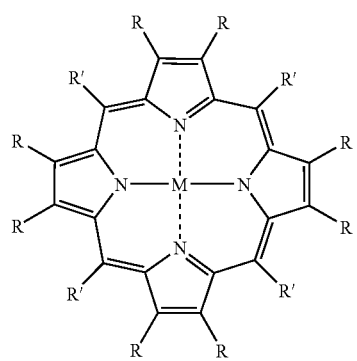

wherein

M is selected from the group consisting of Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Si, Ge, Sn, Pb, P, As, Sb, Bi, S, Se, Te, Po, Cl, Br, I, At, lanthanides, actinides and 2H;

R' is independently selected from the group consisting of a Cl atom, Br atom, I atom, At atom, and a chemical group comprising a valence atom attached to the meso carbon atom of the porphyrin, wherein the valence atom is selected from the group consisting of B, C, N, O, Si, P, S, Ge, As, Se, In, Sn, Sb, Te, Tl, Pb, Bi and Po; and R is independently selected from the group consisting of a Cl atom, Br atom, I atom, At atom, and a chemical group comprising a valence atom attached to a β carbon atom of a pyrrole ring, wherein the valence atom is selected from the group consisting of B, C, N, O, Si, P, S, Ge, As, Se, In, Sn, Sb, Te, Tl, Pb, Bi and Po, alternatively two adjacent R groups attached to the same pyrrole ring together with the two β carbon atoms of the pyrrole ring form a carbocyclic group or heterocyclic group, wherein the organic photosensitive optoelectronic device is a photovoltaic cell.

2. The device of claim 1, wherein the valence atom in at least one R' or R group is C.

3. The device of claim 2, wherein the at least one R' or R group is independently selected from the group consisting of alkyl group, substituted alkyl group, alkenyl group, substituted alkenyl group, alkynyl group, substituted alkynyl group, cycloalkyl group, substituted cycloalkyl group, cycloalkenyl group, substituted cycloalkenyl group, cycloalkynyl group, substituted cycloalkynyl group, aryl group, substituted aryl group, heterocyclic group and substituted heterocyclic group.

4. The device of claim 3, wherein
the substituted alkyl group is an alkyl group substituted with at least one radical independently selected from the group consisting of cycloalkyl groups, cycloalkenyl groups, cycloalkynyl groups, aryl groups, heterocyclic groups, hydroxy group, alkoxy groups, alkenyloxy groups, alkynyloxy groups, cycloalkoxy groups, cycloalkenyoloxy groups, cycloalkynyloxy groups, aryloxy groups, alkylcarbonyloxy groups, cycloalkylcarbonyloxy groups, cycloalkenylcarbonyloxy groups, cycloalkynylcarbonyloxy groups, arylcarbonyloxy groups, thiol group, alkylthio groups, cycloalkylthio groups, cycloalkenylthio groups, cycloalkynylthio groups, arylthio groups, formyl group, acyl groups, carbamoyl groups, amino group, amino groups substituted with at least one alkyl group, alkenyl group or alkynyl group, acylamino groups, N-acyl-N-alkyl amino groups, N-acyl-N-alkenyl amino groups, N-acyl-Nalkynyl amino groups, N-acyl-N-cycloalkyl amino groups, N-acyl-N-cycloalkenyl amino groups, N-acyl-N-aryl amino groups, nitro group, heterocyclic groups and halogen atoms;

the substituted alkenyl group is an alkenyl group substituted with at least one radical independently selected from the group consisting of cycloalkyl groups, cycloalkenyl groups, cycloalkynyl groups, aryl groups, heterocyclic groups, hydroxy group, alkoxy groups, alkenyloxy groups, alkynyloxy groups, cycloalkoxy groups, cycloalkenyoloxy groups, cycloalkynyloxy groups, aryloxy groups, alkylcarbonyloxy groups, cycloalkylcarbonyloxy groups, cycloalkenylcarbonyloxy groups, cycloalkynylcarbonyloxy groups, arylcarbonyloxy groups, thiol group, alkylthio groups, cycloalkylthio groups, cycloalkenylthio groups, cycloalkynylthio groups, arylthio groups, formyl group, acyl groups, carbamoyl groups, amino group, amino groups substituted with at least one alkyl group, alkenyl group or alkynyl group, acylamino groups, N-acyl-N-alkyl amino groups, N-acyl-N-alkenyl amino groups, N-acyl-N-alkynyl amino groups, N-acyl-N-cycloalkyl amino groups, N-acyl-N-cycloalkenyl amino groups, N-acyl-N-aryl amino groups, nitro group, heterocyclic groups and halogen atoms;

the substituted alkynyl group is an alkynyl group substituted with at least one radical independently selected from the group consisting of cycloalkyl groups, cycloalkenyl groups, cycloalkynyl groups, aryl groups, heterocyclic groups, hydroxy group, alkoxy groups, alkenyloxy groups, alkynyloxy groups, cycloalkoxy groups, cycloalkenyoloxy groups, cycloalkynyloxy groups, aryloxy groups, alkylcarbonyloxy groups, cycloalkylcarbonyloxy groups, cycloalkenylcarbonyloxy groups, cycloalkynylcarbonyloxy groups, arylcarbonyloxy groups, thiol group, alkylthio groups, cycloalkylthio groups, cycloalkenylthio groups, cycloalkynylthio groups, arylthio groups, formyl group, acyl groups, carbamoyl groups, amino group, amino groups substituted with at least one alkyl group, alkenyl group or alkynyl group, acylamino groups, N-acyl-N-alkyl amino groups, N-acyl-N-alkenyl amino groups, N-acyl-Nalkynyl amino groups, N-acyl-N-cycloalkyl amino groups, N-acyl-N-cycloalkenyl amino groups, N-acyl-N-aryl amino groups, nitro group, heterocyclic groups and halogen atoms;

the substituted cycloalkyl group is a cycloalkyl group substituted with at least one radical independently selected from the group consisting of alkyl groups, alkenyl groups, alkynyl groups, cycloalkyl groups, cycloalkenyl groups, cycloalkynyl groups, aryl groups, heterocyclic groups, hydroxy group, alkoxy groups, alkenyloxy groups, alkynyloxy groups, cycloalkoxy groups, cycloalkenyoloxy groups, cycloalkynyloxy groups, aryloxy groups, alkylcarbonyloxy groups, cycloalkylcarbonyloxy groups, cycloalkenylcarbonyloxy groups, cycloalkynylcarbonyloxy groups, arylcarbonyloxy groups, thiol group, alkylthio groups, cycloalkylthio groups, cycloalkenylthio groups, cycloalkynylthio groups, arylthio groups, formyl group, acyl groups, carbamoyl groups, amino group, amino groups substituted with at least one alkyl group, alkenyl group or alkynyl group, acylamino groups, N-acyl-N-alkyl amino groups, N-acyl-N-alkenyl amino groups, N-acyl-N-alkynyl amino groups, N-acyl-N-cycloalkyl amino groups, N-acyl-N-cycloalkenyl amino groups, N-acyl-N-aryl amino groups, nitro group, heterocyclic groups and halogen atoms;

the substituted cycloalkenyl group is a cycloalkenyl group substituted with at least one radical independently selected from the group consisting of alkyl groups, alkenyl groups, alkynyl groups, cycloalkyl groups, cycloalkenyl groups, cycloalkynyl groups, aryl groups, heterocyclic groups, hydroxy group, alkoxy groups, alkenyloxy groups, alkynyloxy groups, cycloalkoxy groups, cycloalkenyoloxy groups, cycloalkynyloxy groups, aryloxy groups, alkylcarbonyloxy groups, cycloalkylcarbonyloxy groups, cycloalkenylcarbonyloxy groups, cycloalkynylcarbonyloxy groups, arylcarbonyloxy groups, thiol group, alkylthio groups, cycloalkylthio groups, cycloalkenylthio groups, cycloalkynylthio groups, arylthio groups, formyl group, acyl groups, carbamoyl groups, amino group, amino groups substituted with at least one alkyl group, alkenyl group or alkynyl group, acylamino groups, N-acyl-N-alkyl amino groups, N-acyl-N-alkenyl amino groups, N-acyl-N-alkynyl amino groups, N-acyl-N-cycloalkyl amino groups, N-acyl-N-cycloalkenyl amino groups, N-acyl-N-aryl amino groups, nitro group, heterocyclic groups and halogen atoms;

the substituted cycloalkynyl group is a cycloalkynyl group substituted with at least one radical independently selected from the group consisting of alkyl groups, alkenyl groups, alkynyl groups, cycloalkyl groups, cycloalkenyl groups, cycloalkynyl groups, aryl groups, heterocyclic groups, hydroxy group, alkoxy groups, alkenyloxy groups, alkynyloxy groups, cycloalkoxy groups, cycloalkenyoloxy groups, cycloalkynyloxy groups, aryloxy groups, alkylcarbonyloxy groups, cycloalkylcarbonyloxy groups, cycloalkenylcarbonyloxy groups, cycloalkynylcarbonyloxy groups, arylcarbonyloxy groups, thiol group, alkylthio groups, cycloalkylthio groups, cycloalkenylthio groups, cycloalkynylthio groups, arylthio groups, formyl group, acyl groups, carbamoyl groups, amino group, amino groups substituted with at least one alkyl group, alkenyl group or alkynyl group, acylamino groups, N-acyl-N-alkyl amino groups, N-acyl-N-alkenyl amino groups, N-acyl-N-alkynyl amino groups, N-acyl-N-cycloalkyl amino groups, N-acyl-N-cycloalkenyl amino groups, N-acyl-N-aryl amino groups, nitro group, heterocyclic groups and halogen atoms;

the substituted aryl group is an aryl group substituted with at least one radical independently selected from the group consisting of alkyl groups, alkenyl groups, alkynyl groups, cycloalkyl groups, cycloalkenyl groups, cycloalkynyl groups, aryl groups, heterocyclic groups, hydroxy group, alkoxy groups, alkenyloxy groups, alkynyloxy groups, cycloalkoxy groups, cycloalkenyoloxy groups, cycloalkynyloxy groups, aryloxy groups, alkylcarbonyloxy groups, cycloalkylcarbonyloxy groups, cycloalkenylcarbonyloxy groups, cycloalkynylcarbonyloxy groups, arylcarbonyloxy groups, thiol group, alkylthio groups, cycloalkylthio groups, cycloalkenylthio groups, cycloalkynylthio groups, arylthio groups, formyl group, acyl groups, carbamoyl groups, amino group, amino groups substituted with at least one alkyl group, alkenyl group or alkynyl group, acylamino groups, N-acyl-N-alkyl amino groups, N-acyl-N-alkenyl amino groups, N-acyl-N-alkynyl amino groups, N-acyl-N-cycloalkyl amino groups, N-acyl-N-cycloalkenyl amino groups, N-acyl-N-aryl amino groups, nitro group, heterocyclic groups and halogen atoms; and the substituted heterocyclic group is a heterocyclic group substituted with at least one radical independently selected from the group consisting of alkyl groups, alkenyl groups, alkynyl groups, cycloalkyl groups, cycloalkenyl groups, cycloalkynyl groups, aryl groups, heterocyclic groups, hydroxy group, alkoxy groups, alkenyloxy groups, alkynyloxy groups, cycloalkoxy groups, cycloalkenyoloxy groups, cycloalkynyloxy groups, aryloxy groups, alkylcarbonyloxy groups, cycloalkylcarbonyloxy groups, cycloalkenylcarbonyloxy groups, cycloalkynylcarbonyloxy groups, arylcarbonyloxy groups, thiol group, alkylthio groups, cycloalkylthio groups, cycloalkenylthio groups, cycloalkynylthio groups, arylthio groups, formyl group, acyl groups, carbamoyl groups, amino group, amino groups substituted with at least one alkyl group, alkenyl group or alkynyl group, acylamino groups, N-acyl-N- alkyl amino groups, N-acyl-N-alkenyl amino groups, N-acyl-N-alkynyl amino groups, N-acyl-N-cycloalkyl amino groups, N-acyl-N-cycloalkenyl amino groups, N-acyl-N-aryl amino groups, nitro group, heterocyclic groups and halogen atoms.

5. The device of claim 3, wherein the substituted alkyl group is selected from the group consisting of aralkyl group, cycloalkyl substituted alkyl group, cycloalkenyl substituted alkyl group, hydroxyl substituted alkyl group, alkoxy substituted alkyl group, cycloalkoxy substituted alkyl group, aryloxy substituted alkyl group, alkylcarbonyloxy substituted alkyl group, cycloalkylcarbonyloxy substituted alkyl group, cycloalkenylcarbonyloxy substituted alkyl group, cycloalkynylcarbonyloxy substituted alkyl group, arylcarbonyloxy substituted alkyl group, thiol substituted alkyl group, alkylthio substituted alkyl group, cycloalkylthio substituted alkyl group, formyl substituted alkyl group, acylated alkyl group, carbamoyl substituted alkyl group, amino substituted alkyl group, acylamino substituted alkyl group, nitro substituted alkyl group, halogen substituted alkyl group and heterocyclyl substituted alkyl group;

the substituted alkenyl group is selected from the group consisting of aralkenyl group, cycloalkenyl substituted alkenyl group, cycloalkenyl substituted alkenyl group, hydroxyl substituted alkenyl group, alkoxy substituted alkenyl group, cycloalkoxy substituted alkenyl group, aryloxy substituted alkenyl group, alkylcarbonyloxy substituted alkenyl group, cycloalkylcarbonyloxy substituted alkenyl group, cycloalkenylcarbonyloxy substituted alkenyl group, cycloalkynylcarbonyloxy substituted alkenyl group, arylcarbonyloxy substituted alkenyl group, thiol substituted alkenyl group, alkylthio substituted alkenyl group, cyclo alkylthio substituted alkenyl group, formyl substituted alkenyl group, acylated alkenyl group, carbamoyl substituted alkenyl group, amino substituted alkenyl group, acylamino substituted alkenyl group, nitro substituted alkenyl group, halogen substituted alkenyl group and heterocyclyl substituted alkenyl group;

the substituted alkynyl group is selected from the group consisting of aralkynyl group, cycloalkyl substituted alkynyl group, cycloalkenyl substituted alkynyl group, hydroxyl substituted alkynyl group, alkoxy substituted alkynyl group, cycloalkoxy substituted alkynyl group, aryloxy substituted alkynyl group, alkylcarbonyloxy substituted alkynyl group, cycloalkylcarbonyloxy substituted alkynyl group, cycloalkenylcarbonyloxy substituted alkynyl group, cycloalkynylcarbonyloxy substituted alkynyl group, arylcarbonyloxy substituted alkynyl group, thiol substituted alkynyl group, alkylthio substituted alkynyl group, cycloalkylthio substituted alkynyl group, formyl substituted alkynyl group, acylated alkynyl group, carbamoyl substituted alkynyl group, amino substituted alkynyl group, acylamino substituted alkynyl group, nitro substituted alkynyl group, halogen substituted alkynyl group and heterocyclyl substituted alkynyl group;

the substituted cycloalkyl group is selected from the group consisting of alkyl substituted cycloalkyl group, aryl substituted cycloalkyl group, cycloalkyl substituted cycloalkyl group, cycloalkenyl substituted cycloalkyl group, cycloalkynyl substituted cycloalkyl group, hydroxyl substituted cycloalkyl group, alkoxy substituted cycloalkyl group, cycloalkoxy substituted cycloalkyl group, aryloxy substituted cycloalkyl group, alkylcarbonyloxy substituted cycloalkyl group, cycloalkylcarbonyloxy substituted cycloalkyl group, cycloalkenylcarbonyloxy substituted cycloalkyl group, cycloalkynylcarbonyloxy substituted cycloalkyl group, arylcarbonyloxy substituted cycloalkyl group, thiol substituted cycloalkyl group, alkylthio substituted cycloalkyl group, cycloalkylthio substituted cycloalkyl group, formyl substituted cycloalkyl group, acylated cycloalkyl group, carbamoyl substituted cycloalkyl group, amino substituted cycloalkyl group, acylamino substituted cycloalkyl group, nitro substituted cycloalkyl group, halogen substituted cycloalkyl group and heterocyclyl substituted cycloalkyl group;

the substituted cycloalkenyl group is selected from the group consisting of alkyl substituted cycloalkenyl group, aryl substituted cycloalkenyl group, cycloalkyl substituted cycloalkenyl group, cycloalkenyl substituted cycloalkenyl group, cycloalkynyl substituted cycloalkenyl group, hydroxyl substituted cycloalkenyl group, alkoxy substituted cycloalkenyl group, cycloalkoxy substituted cycloalkenyl group, aryloxy substituted cycloalkenyl group, alkylcarbonyloxy substituted cycloalkenyl group, cycloalkylcarbonyloxy substituted cycloalkenyl group, cycloalkenylcarbonyloxy substituted cycloalkenyl group, cycloalkynylcarbonyloxy substituted cycloalkenyl group, arylcarbonyloxy substituted cycloalkenyl group, thiol substituted cycloalkenyl group, alkylthio substituted cycloalkenyl group, cycloalkylthio substituted cycloalkenyl group, formyl substituted cycloalkenyl group, acylated cycloalkenyl group, carbamoyl substituted cycloalkenyl group, amino substituted cycloalkenyl group, acylamino substituted cycloalkenyl group, nitro substituted cycloalkenyl group, halogen substituted cycloalkenyl group and heterocyclyl substituted cycloalkenyl group;

the substituted cycloalkynyl group is selected from the group consisting of alkyl substituted cycloalkynyl group, aryl substituted cycloalkynyl group, cycloalkyl substituted cycloalkynyl group, cycloalkenyl substituted cycloalkynyl group, cycloalkynyl substituted cycloalkynyl group, hydroxyl substituted cycloalkynyl group, alkoxy substituted cycloalkynyl group, cycloalkoxy substituted cycloalkynyl group, aryloxy substituted cycloalkynyl group, alkylcarbonyloxy substituted cycloalkynyl group, cycloalkylcarbonyloxy substituted cycloalkynyl group, cycloalkenylcarbonyloxy substituted cycloalkynyl group, cycloalkynylcarbonyloxy substituted cycloalkynyl group, arylcarbonyloxy substituted cycloalkynyl group, thiol substituted cycloalkynyl group, alkylthio substituted cycloalkynyl group, cycloalkylthio substituted cycloalkynyl group, formyl substituted cycloalkynyl group, acylated cycloalkynyl group, carbamoyl substituted cycloalkynyl group, amino substituted cycloalkynyl group, acylamino substituted cycloalkynyl group, nitro substituted cycloalkynyl group, halogen substituted cycloalkynyl group and heterocyclyl substituted cycloalkynyl group;

the substituted aryl group is selected from the group consisting of alkyl substituted aryl group, aryl substituted aryl group, cycloalkyl substituted aryl group, cycloalkenyl substituted aryl group, cycloalkynyl substituted aryl group, hydroxyl substituted aryl group, alkoxy substituted aryl group, cycloalkoxy substituted aryl group, aryloxy substituted aryl group, alkylcarbonyloxy substituted aryl group, cycloalkylcarbonyloxy substituted aryl group, cycloalkenylcarbonyloxy substituted aryl group, cycloalkynylcarbonyloxy substituted aryl group, arylcarbonyloxy substituted aryl group, thiol substituted aryl group, alkylthio substituted aryl group, cycloalkylthio substituted aryl group, formyl substituted aryl group, acylated aryl group, carbamoyl substituted aryl group, amino substituted aryl group, acylamino substituted aryl group, nitro substituted aryl group, halogen substituted aryl group and heterocyclyl substituted aryl group; and the substituted heterocyclic group is selected from the group consisting of alkyl substituted heterocyclic group, aryl substituted heterocyclic group, cycloalkyl substituted heterocyclic group, cycloalkenyl substituted heterocyclic group, cycloalkynyl substituted heterocyclic group, hydroxyl substituted heterocyclic group, alkoxy substituted heterocyclic group, cycloalkoxy substituted heterocyclic group, aryloxy substituted heterocyclic group, alkylcarbonyloxy substituted heterocyclic group, cycloalkylcarbonyloxy substituted heterocyclic group, cycloalkenylcarbonyloxy substituted heterocyclic group, cycloalkynylcarbonyloxy substituted heterocyclic group, arylcarbonyloxy substituted heterocyclic group, thiol substituted heterocyclic group, alkylthio substituted heterocyclic group, cycloalkylthio substituted heterocyclic group, formyl substituted heterocyclic group, acylated heterocyclic group, carbamoyl substituted heterocyclic group, amino substituted heterocyclic group, acylamino substituted heterocyclic group, nitro substituted heterocyclic group, halogen substituted heterocyclic group and heterocyclyl substituted heterocyclic group.

6. The device of claim 3, wherein the at least one R' or R group is independently selected from the group consisting of alkyl groups, alkenyl groups, alkynyl groups, cycloalkyl groups, cycloalkenyl groups, cycloalkynyl groups, aryl groups and heterocyclic groups.

7. The device of claim 3, wherein the alkyl group is a $C_1$-$C_6$ alkyl group; the substituted alkyl group is a substituted $C_1$-$C_6$ alkyl group; the alkenyl group is a $C_2$-$C_6$ alkenyl group; the substituted alkenyl group is a substituted $C_2$-$C_6$ alkenyl group; the alkynyl group is a $C_2$-$C_6$ alkynyl group; the substituted alkynyl group is a substituted $C_2$-$C_6$ alkynyl group; the cycloalkyl group is a $C_3$-$C_8$ cycloalkyl group; the substituted cycloalkyl group is a substituted $C_3$-$C_8$ cycloalkyl group; the cycloalkenyl group is a $C_3$-$C_8$ cycloalkenyl group the substituted cycloalkenyl group is a substituted $C_3$-$C_8$ cycloalkenyl group; the cycloalkynyl group is a $C_3$-$C_8$ cycloalkynyl group; the substituted cycloalkynyl group is a substituted $C_3$-$C_8$ cycloalkynyl group; the aryl group is a $C_6$-$C_{10}$ aryl group; the substituted aryl group is a substituted $C_6$-$C_{10}$ aryl group; the heterocyclic group is a cyclic group comprising a 4-, 5-, 6-, 7- or 8-membered ring, wherein the ring comprises at least one ring atom selected from the group consisting of N, O and S with C as the remaining ring atom(s); and the substituted heterocyclic group is a substituted cyclic group comprising a 4-, 5-, 6-, 7- or 8-membered ring and at least one ring atom selected group the group consisting of N, O and S with C as the remaining ring atom(s).

8. The device of claim 3, wherein the cycloalkyl group, substituted cycloalkyl group, cycloalkenyl group, substituted cycloalkenyl group, cycloalkynyl group, substituted cycloalkynyl group, aryl group, substituted aryl group, heterocyclic group and substituted heterocyclic group are independently monocyclic or multicyclic.

9. The device of claim 8, wherein the cycloalkyl group, substituted cycloalkyl group, cycloalkenyl group, substituted cycloalkenyl group, cycloalkynyl group, substituted cycloalkynyl group, aryl group, substituted aryl group, heterocyclic group and substituted heterocyclic group are monocyclic.

10. The device of claim 8, wherein the cycloalkyl group, substituted cycloalkyl group, cycloalkenyl group, substituted cycloalkenyl group, cycloalkynyl group, substituted cycloalkynyl group, aryl group, substituted aryl group, heterocyclic group and substituted heterocyclic group are multicyclic.

11. The device of claim 7, wherein the heterocyclic group is selected from the group consisting of pyrrolidinyl group, piperidinyl group, piperazinyl group, morpholino group, thiomorpholino group, homopiperidinyl group, chromanyl group, isochromanyl group, chromenyl group, pyrrolyl group, furanyl group, thienyl group, pyrazolylgroup, imidazolyl group, furazanyl group, oxazolyl group, isoxazolyl group, thiazolyl group, isothiazolyl group, pyridyl group, pyridazinyl group, pyrimidinyl group, pyrazinyl group, pyranyl group, indolyl group, isoindolyl group, indazolyl group, purinyl group, indolizinyl group, quinolinyl group, isoquinolinyl group, quinazolinyl group, pteridinyl group, quinolizinyl group, benzoxazinyl group, carbazolyl group, phenazinyl group, phenothiazinyl group and phenanthridinyl group; and the substituted heterocyclic group is a substituted pyrrolidinyl group, piperidinyl group, piperazinyl group, morpholino group, thiomorpholino group, homopiperidinyl group, chromanyl group, isochromanyl group, chromenyl group, pyrrolyl group, furanyl group, thienyl group, pyrazolyl group, imidazolyl group, furazanyl group, oxazolyl group, isoxazolyl group, thiazolyl group, isothiazolyl group, pyridyl group, pyridazinyl group, pyrimidinyl group, pyrazinyl group, pyranyl group, indolyl group, isoindolyl group, indazolyl group, purinyl group, indolizinyl group, quinolinyl group, isoquinolinyl group, quinazolinyl group, pteridinyl group, quinolizinyl group, benzoxazinyl group, carbazolyl group, phenazinyl group, phenothiazinyl group or phenanthridinyl group.

12. The device of claim 1, wherein two adjacent R groups of at least one pyrrole ring together with the two β carbon atoms of the at least one pyrrole ring form a carbocyclic group, substituted carbocyclic group, heterocyclic group or substituted heterocyclic group.

13. The device of claim 12, wherein the two adjacent R groups of the at least one pyrrole ring together with the two β carbon atoms of the at least one pyrrole ring form a carbocyclic group or substituted carbocyclic group.

14. The device of claim 13, wherein the carbocyclic group or substituted carbocyclic group is monocyclic.

15. The device of claim 13, wherein the carbocyclic group or substituted carbocyclic group is multicyclic.

16. The device of claim 13, wherein the carbocyclic group or substituted carbocyclic group is a macrocycle or benzanulated π-system.

17. The device of claim 13, wherein the carbocyclic group or substituted carbocyclic group is aromatic.

18. The device of claim 12, wherein the two adjacent R groups of the at least one pyrrole ring together with the two β carbon atoms of the at least one pyrrole ring form a heterocyclic group or substituted heterocyclic group.

19. The device of claim 18, wherein the heterocyclic group or substituted heterocyclic group is monocyclic.

20. The device of claim 18, wherein the heterocyclic group or substituted heterocyclic group is multicyclic.

21. The device of claim 18, wherein the heterocyclic group or substituted heterocyclic group is aromatic.

22. The device of claim 2, wherein the at least one R' or R group is alkyl, substituted alkyl, aryl or substituted aryl.

23. The device of claim 22, wherein the at least one R' or R group is phenyl, tolyl, xylenyl, mesityl, methyl, ethyl, n-propyl or isopropyl.
24. The device of claim 1, wherein the at least one nonplanar porphyrin of formula (1) is selected from compounds represented by the following formulae:
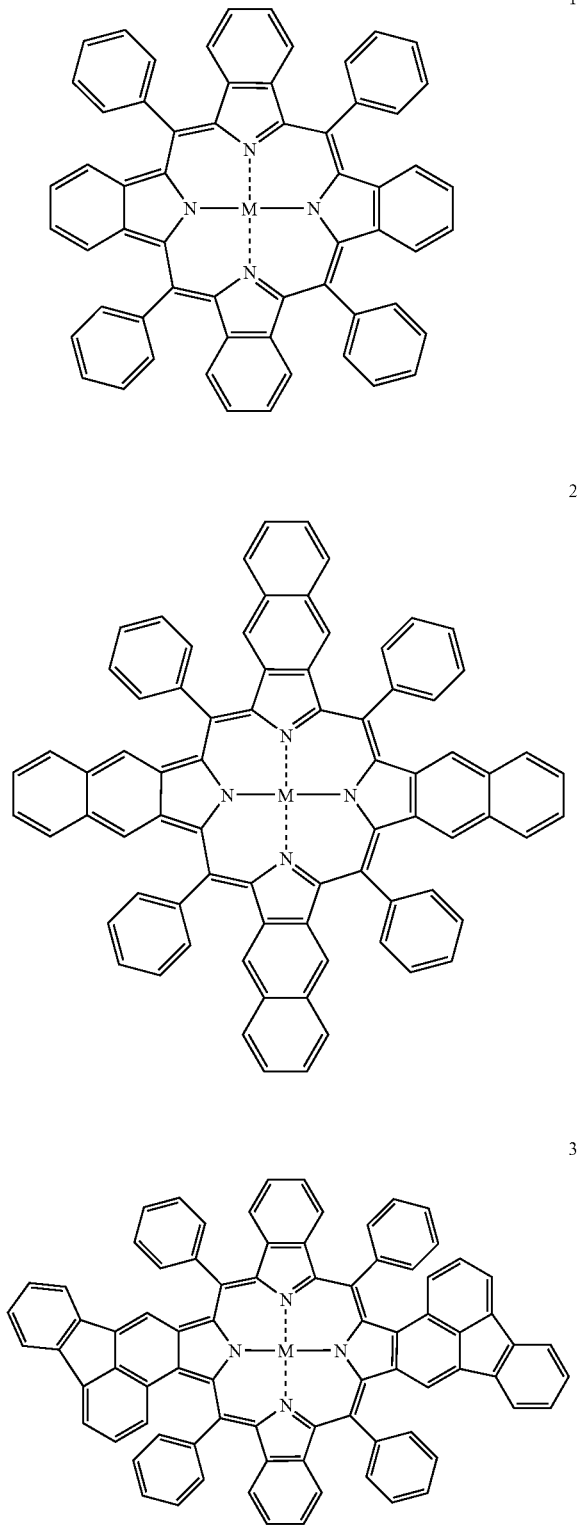
-continued
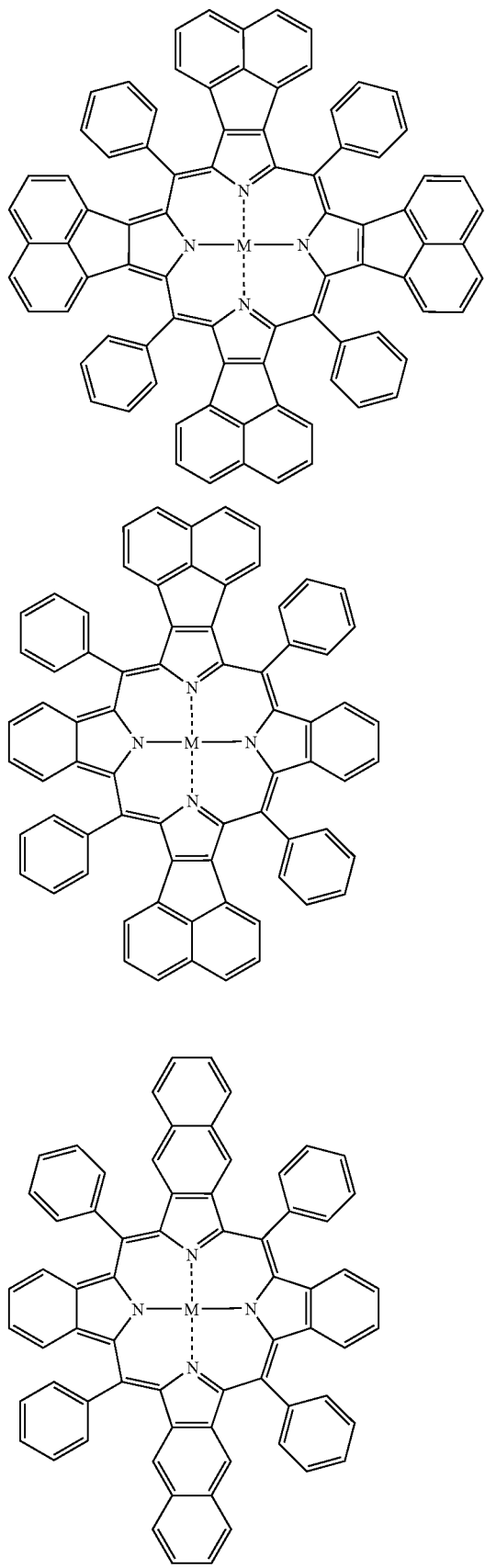

-continued

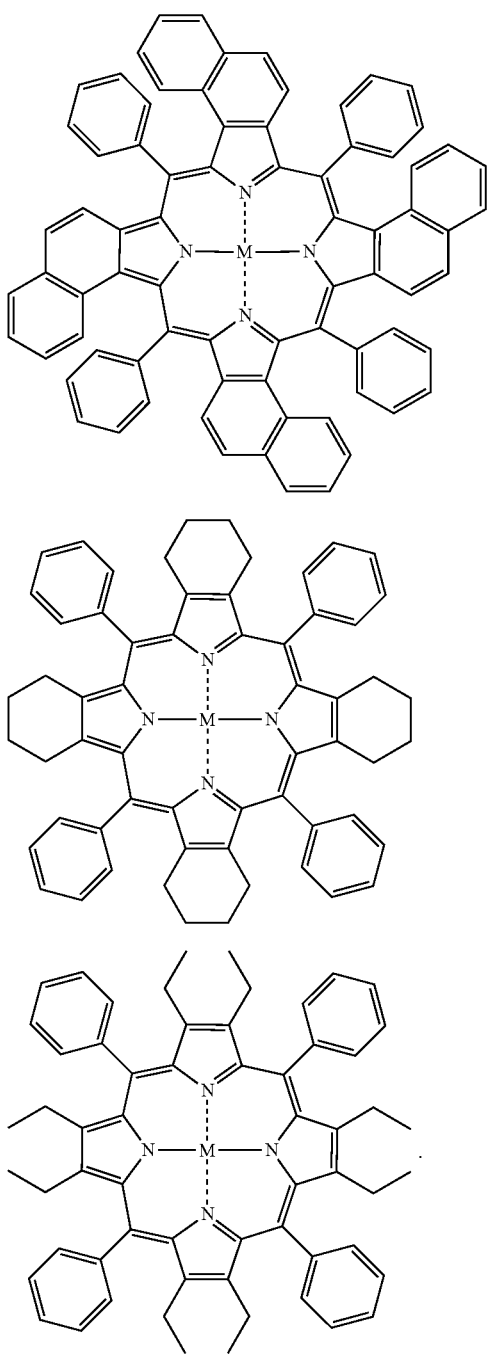

25. The device of claim 1, wherein the valence atom in at east one R' or R group is O.

26. The device of claim 25, wherein the at least one R' or R group having O as the valence atom is hydroxy, alkoxy, alkenyloxy, alkynyloxy, cycloakoxy, cycloalkenyloxy, cycloalknyloxy, aralkyloxy, aralkenyloxy, aralkynyloxy, aryloxy, alkylcarbonyloxy, alkenylcarbonyloxy, alkynylcarbonyloxy, hydroxycarbonyloxy or alkoxycarbonyloxy.

27. The device of claim 26, wherein the at least one R' or R group having O as the valence atom is hydroxy or alkoxy.

28. The device of claim 27, wherein the at least one R' or R group having O as the valence atom is OH, methoxy, ethoxy, n-propoxy or isopropoxy.

29. The device of claim 1, wherein at least one R or R' group is independently selected from the group consisting of a Cl atom, Br atom, I atom and At atom.

30. The device of claim 1, wherein at least one R or R' group has N as the valence atom.

31. The device of claim 30, wherein the at least one R or R' group having N as the valence atom is selected from the group consisting of amino group, alkylamino groups, dialkylamino groups, alkenylamino groups, dialkenylamino groups, alkynylamino groups, dialkynylamino groups, N-alkyl-N-alkenylamino groups, N-alkyl-N-alkynylamino groups, N-alkenyl-N-alkynylamino groups, acylamino groups, N-acyl-N-alkyl amino groups, N-acyl-N-alkenyl amino groups, N-acyl-N-alkynyl amino groups, N-acyl-N-cycloalkyl amino groups, N-acyl-N-cycloalkenyl amino groups, N-acyl-N-aryl amino groups, nitro group, heterocyclic groups comprising a nitrogen valence atom and substituted heterocyclic groups comprising a nitrogen valence atom.

32. The device of claim 1, wherein at least one R or R' group has S as the valence atom.

33. The device of claim 32, wherein the at least one R or R' group comprising S as the valence atom is selected from the group consisting of thiol group, alkylthio groups, alkenylthio groups, alkynylthio groups, aralkylthio groups, aralkenylthio groups, aralkynylthio groups, cycloalkylalkylthio groups, cycloalkenylalkylthio groups, cycloalkynylalkylthio groups, cycloalkylthio groups, cycloalkenylthio groups, cycloalkynylthio groups, and arylthio groups.

34. The device of claim 1, wherein M is Pt, Pd or Ir.

35. The device of claim 34, wherein M is Pt.

36. The device of claim 34, wherein M is Pd.

37. The device of claim 35, wherein the at least one nonplanar porphyrin is Pt(tetraphenyl benzo-porphyrin).

38. The device of claim 36, wherein the at east one nonplanar porphyrin is Pd(tetraphenyl benzo-porphyrin).

39. The device of claim 1, wherein the device is an organic photovoltaic cell.

40. The device of claim 1, wherein the device is a photoconductor cell.

41. The device of claim 1, wherein the device is a photodetector.

42. The device of claim 1, wherein the device comprises a donor material and an acceptor material, and wherein the donor material comprises the at least one nonplanar porphyrin.

43. The device of claim 1, wherein the device comprises a donor material and an acceptor material, and wherein the acceptor material comprises the at least one nonplanar porphyrin.

44. The device of claim 1, wherein the device comprises a donor material and an acceptor material, and wherein the donor material comprises a nonplanar porphyrin of formula (I) and the acceptor material comprises another nonplanar porphyrin of formula (I).

45. The device of claim 42, wherein the acceptor material comprises $C_{60}$.

46. A method for fabricating an organic photosensitive device, comprising providing a donor material and an acceptor material, wherein the donor material and/or the acceptor material comprises at least one nonplanar porphyrin of formula (I),

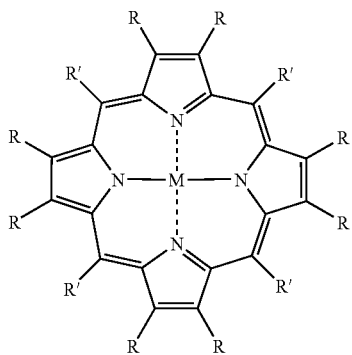

(I)

wherein

M is selected from the group consisting of Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, n, Si, Ge, Sn, Pb, P, As, Sb, Bi, S, Se, Te, Po, Cl, Br, I, At, lanthanides, actinides and 2H;

R' is independently selected from the group consisting of a Cl atom, Br atom, I atom, At atom, and a chemical group comprising a valence atom attached to the meso carbon atom of the porphyrin, wherein the valence atom is selected from the group consisting of B, C, N, O, Si, P, S, Ge, As, Se, In, Sn, Sb, Te, Tl, Pb, Bi and Po; and R is independently selected from the group consisting of a Cl atom, Br atom, I atom, At atom, and a chemical group comprising a valence atom attached to a β carbon atom of a pyrrole ring, wherein the valence atom is selected from the group consisting of B, C, N, O, Si, P, S, Ge, As, Se, In, Sn, Sb, Te, Tl, Pb, Bi and Po, alternatively two adjacent R groups attached to the same pyrrole ring together with the two β carbon atoms of the pyrrole ring form a carbocyclic group or heterocyclic group; and making the organic photosensitive optoelectronic device comprising putting the donor material in contact with the acceptor material, wherein when both the donor material and acceptor material comprise at least one nonplanar porphyrin of formula (I), the at least one nonplanar porphyrin in the donor material is different from the at least one nonplanar porphyrin in the acceptor material.

* * * * *